(12) United States Patent
Woltering

(10) Patent No.: US 8,927,535 B2
(45) Date of Patent: Jan. 6, 2015

(54) CYCLOPROPYL-FUSED-1,3-THIAZEPINES AS BACE1 AND/OR BACE2 INHIBITORS

(75) Inventor: Thomas Woltering, Freiburg (DE)

(73) Assignee: Hoffman-La Roche Inc., Nutley, NJ (US)

(*) Notice: Subject to any disclaimer, the term of this patent is extended or adjusted under 35 U.S.C. 154(b) by 232 days.

(21) Appl. No.: 13/537,118

(22) Filed: Jun. 29, 2012

(65) Prior Publication Data

US 2013/0012494 A1  Jan. 10, 2013

(30) Foreign Application Priority Data

Jul. 6, 2011 (EP) .................................. 11172784

(51) Int. Cl.
*A61K 31/554* (2006.01)
*C07D 417/12* (2006.01)

(52) U.S. Cl.
CPC .................. *C07D 417/12* (2013.01)
USPC ...................... 514/211.09; 540/546

(58) Field of Classification Search
CPC ........................ A61K 31/554; C07D 417/12
USPC ...................... 514/211.09; 540/546
See application file for complete search history.

(56) References Cited

FOREIGN PATENT DOCUMENTS

WO  2011/005738  1/2011
WO  2011.029803  3/2011

OTHER PUBLICATIONS (International Search Report PCT/EP2012/062867 Aug. 1, 2012).
Lagos et al., "Blood" 109(4):1550-1558 ( 2007).
Woodard-Grice et al., "J. Biol. Chem." 283(39):26364-26373 ( 2008).
Kuhn et al., "J. Biol. Chem." 282(16):11982-11995 ( 2007).
Fukui et al., Cell Metab. 2:373-384 ( 2005).
Akpinar et al., Cell Metab. 2:385-397 ( 2005).
Luo et al., "Nature Neuroscience" 3:231-232 ( 2001).
Finzi et al., "Ultrastruct. Pathol." 32(6):246-251 ( 2008).
Koistinen et al., "Muscle & Nerve" 34(4):444-450 ( 2006).
Hodges et al., Hum. Mol. Genet. 15:965-977 ( 2006).
Talantov et al., Clin. Cancer Res. 11:7234-7242 ( 2005).
Toegel et al., "Osteoarthritis & Cartilage" 18(2):240-248 ( 2010).
Vassar et al., BACE, Science 286:735 ( 1999).
Sugimoto et al., "J. Biol. Chem." 282(48):34896-34903 ( 2007).
Roberds et al., Hum. Mol. Genet. 10(12):1317-1324 ( 2001).
Hedlund et al., Cancer Research 68(2):388-394 ( 2008).
Desnues et al., Clin. Vaccine Immunol. 13:170-178 ( 2006).
Selkoe et al., "Annual Review Cell Biology" 10:373-403 ( 1994).
Basset et al., Scand. J. Immunol. 51:307-311 ( 2000).
Prentki et al., J. Clin. Investig. 116(7):1802-1812 ( 2006).
Kiljanski et al., "Thyroid" 15(7):645-652 ( 2005).
Gatchel et al., Proc. Natl. Acad. Sci. USA 105:1291-1296 ( 2008).
Kim et al., "Neurobiology of Disease" 22(2):346-356 ( 2006).
Hussain et al., "Molecular & Cellular Neurosciences" 16:609-619 ( 2000).
McConlogue et al., "J. Biol. Chem." 282(36):26326-26334 ( 2007).
Greenberg et al., "Annals of Neurology" 57(5):664-678 ( 2005).
Kondoh et al., "Breast Cancer & Research Treatment" 78(1):37-44 ( 2003).
Zimmet et al., Nature 414:782-787 ( 2001).
Kihara et al., Proc. Natl. Acad. Sci. USA 106:21807-21812 ( 2009).
Hoffmeister et al., JOP 10(5):502-506 ( 2009).
Hardy et al., "Science" ((5580)), 297:353-356, 2002.
Li et al., "Aging Cell" 5(2):153-165 ( 2006).
Barbiero et al., Exp. Neurol. 182:335-345 ( 2003).
Baggio et al., Annu. Rev. Med. 57:265-281 ( 2006).
Maugeri et al., "Srp Arh Celok Lek—Abstract" 138:50-52 ( 2010).
Wild et al., "Diabetes Care" 27(5):1047-1053 ( 2004).
Merten et al., "Zeitschrift fur Kardiologie" ((English language Summary is attached to the reference)), 93(11):855-863 ( 2004).
Grewal et al., Mol. Cell Biol. 26:4970-4981 ( 2006).
Vattemi et al., "Lancet" ((9297)), 358:1962-1964 ( 2001).
Lichtenthaler et al., "J. Biol. Chem." 278(49):48713-48719 ( 2003).

*Primary Examiner* — Brenda Coleman

(57) ABSTRACT

The present invention provides cyclopropyl-fused-1,3-thiazepines of formula I

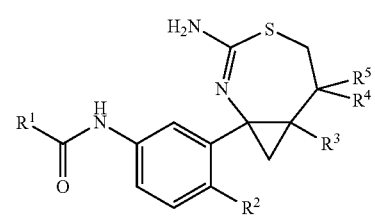

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

13 Claims, No Drawings

CYCLOPROPYL-FUSED-1,3-THIAZEPINES AS BACE1 AND/OR BACE2 INHIBITORS

PRIORITY TO RELATED APPLICATION(S)

This application claims the benefit of European Patent Application No. 11172784.8, filed Jul. 6, 2011, which is hereby incorporated by reference in its entirety.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 July 19; 297(5580:353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knockout mice are healthy despite lacking the primary beta-secretase activity in brain: implications for Alzheimer's disease therapeutics, *Hum Mol Genet*. 2001 Jun. 1; 10(12): 1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem*. 2007 Sep. 7; 282(36):26326). It is thus presumed that inhibitors of BACE1 activity can be useful agents for therapeutic intervention in Alzheimer's disease (AD).

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, K G M M Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (LL Baggio & D J Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients.

Inhibitors of BACE1 and/or BACE2 can in addition be used to treat the following diseases:
IBM (inclusion body myositis) (Vattemi G. et al., Lancet. 2001 Dec. 8; 358(9297):1962-4), Down's Syndrome (Barbiero L. et al, Exp Neurol. 2003 August; 182(2):335-45), Wilson's Disease (Sugimoto I. et al., J Biol Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., Proc Natl Acad Sci USA 2008 Jan. 29; 105(4):1291-6), Dermatomyositis (Greenberg S. A. et al., Ann Neurol. 2005 May; 57(5):664-78 and Greenberg S. A. et al., Neurol 2005 May; 57(5):664-78), Kaposi Sarcoma (Lagos D. et al, Blood, 2007 Feb. 15; 109(4):1550-8), Glioblastoma multiforme (E-MEXP-2576, http://www.ebi.ac.uk/microarray-as/aer/result?queryFor=PhysicalArrayDesign&aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2):346-56. Epub 2006 Jan. 19 and Hodges A. et al., Hum Mol Genet. 2006 Mar. 15; 15(6):965-77. Epub 2006 Feb. 8), Multiple Mieloma (Kihara Y. et al, Proc Natl Acad Sci USA. 2009 Dec. 22; 106(51):21807-12), Malignant melanoma (Talantov D. et al, Clin Cancer Res. 2005 Oct. 15; 11(20):7234-42), Sjogren syndrome (Basset C. et al., Scand J Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol Chem. 2008 Sep. 26; 283(39):26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

FIELD OF THE INVENTION

The present invention provides cyclopropyl-fused-1,3-thiazepines having BACE1 and/or BACE2 inhibitory properties, their manufacture, pharmaceutical compositions containing them and their use as therapeutically active substances.

SUMMARY OF THE INVENTION

The present invention provides selective BACE2 inhibitors. The present invention provides novel compounds of formula I and pharmaceutical compositions containing them. The invention also provides methods for the manufacture of the compounds and compositions of the invention.

Compounds of the invention are useful as therapeutically active substances, particularly in the treatment and/or prevention of diseases which are associated with the inhibition of BACE2. Furthermore, the formation, or formation and deposition, of β-amyloid peptides in, on or around neurological tissue (e.g., the brain) are inhibited by the present compounds, i.e. inhibition of the Aβ-production from APP or an APP fragment.

The invention further provides methods for treatment, e.g. control or prevention, of illnesses such as Alzheimer's disease and type 2 diabetes. Furthermore, the invention provides methods for the treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease and Wilson's Disease. The novel compounds of formula I have improved pharmacological properties.

The present invention provides a compound of formula I,

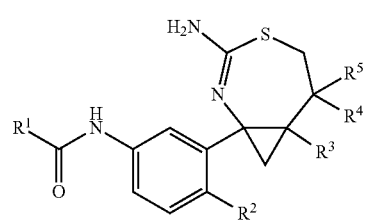

wherein the substituents and variables are as described below and in the claims, or a pharmaceutically acceptable salt thereof.

The present compounds have Asp2 (β-secretase, BACE1 or Memapsin-2) inhibitory activity and/or BACE2 inhibitory activity. The present compounds having Asp2 (β-secretase, BACE1 or Memapsin-2) inhibitory activity can be used in the therapeutic and/or prophylactic treatment of diseases and disorders characterized by elevated β-amyloid levels and/or β-amyloid oligomers and/or β-amyloid plaques and further deposits, particularly Alzheimer's disease. The present compounds having BACE2 inhibitory activity can be used in the therapeutic and/or prophylactic treatment of diseases and disorders such as type 2 diabetes and other metabolic disorders.

DETAILED DESCRIPTION OF THE INVENTION

The present invention provides compounds of formula I and their pharmaceutically acceptable salts, the preparation of the above mentioned compounds, pharmaceutical compositions containing them and methods for the manufacture of the compounds and compositions of the invention. The invention also provides methods for the therapeutic and/or prophylactic treatment of diseases and disorders which are associated with inhibition of BACE1 and/or BACE2 activity, such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which can be linear or branched, with single or multiple branching, wherein the alkyl group contains 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" groups are "$C_{1-3}$-alkyl". Specific groups are methyl and ethyl—particularly methyl.

The term "cyano-$C_{1-6}$-alkyl", alone or in combination with other groups, refers to $C_{1-6}$-alkyl as defined herein, which is substituted by one or multiple cyano groups, in particular 1-5 cyano groups, more particular one cyano group. Examples are cyano-methyl and the like.

The term "halogen-$C_{1-6}$-alkyl", alone or in combination with other groups, refers to $C_{1-6}$-alkyl as defined herein, which is substituted by one or multiple halogen atoms, in particular 1-5 halogen atoms, more particular 1-3 halogen atoms, most particular one halogen atom or three halogen atom. The term "halogen-$C_{1-3}$-alkyl", alone or in combination with other groups, refers to $C_{1-3}$-alkyl as defined herein, which is substituted by one or multiple halogen atoms, in particular 1-5 halogen atoms, more particular 1-3 halogen atoms, most particular one halogen atom or three halogen atom. A particular halogen is fluoro. A particular "halogen-$C_{1-6}$-alkyl" is fluoro-$C_{1-6}$-alkyl, and a particular "halogen-$C_{1-3}$-alkyl" is fluoro-$C_{1-3}$-alkyl. Examples are difluoromethyl, chloromethyl, fluoromethyl and the like. A specific group is trifluoromethyl.

The term "$C_{1-6}$-alkoxy-$C_{1-6}$-alkyl", alone or in combination with other groups, refers to $C_{1-6}$-alkyl, which is substituted by one or multiple $C_{1-6}$-alkoxy as defined herein. Examples are MeO-Me, 1MeO-Et, 2MeO-Et, 1MeO-2EtO-propyl and the like.

The term "cyano", alone or in combination with other groups, refers to N≡C—.

The term "halogen", alone or in combination with other groups, denotes chloro (Cl), iodo (I), fluoro (F) and bromo (Br). Particular "halogen" groups are Cl and F. A specific group is F.

The term "heteroaryl", alone or in combination with other groups, refers to an aromatic group having a single 4 to 8 membered ring or multiple condensed rings containing 6 to 14, in particular 6 to 10, ring atoms and containing 1, 2 or 3 heteroatoms individually selected from N, O and S, in particular N and O, in which group at least one heterocyclic ring is aromatic. Examples of "heteroaryl" groups include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. A particular "heteroaryl" group is pyridinyl. A specific group is pyridine-2-yl.

The term "$C_{1-6}$-alkoxy", alone or in combination with other groups, stands for an —O—$C_{1-6}$-alkyl radical which can be linear or branched, with single or multiple branching, wherein the alkyl group contains 1 to 6 carbon atoms, for example, methoxy (OMe), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. A specific group is methoxy.

The term "halogen-$C_{1-6}$-alkoxy", alone or in combination with other groups, refers to $C_{1-6}$-alkoxy as defined herein, which is substituted by one or multiple halogen atoms, in particular fluoro. A particular "halogen-$C_{1-6}$-alkoxy" is fluoro-$C_{1-6}$-alkoxy. Specific examples are difluoromethoxy and trifluoromethoxy.

The term "$C_{2-6}$-alkynyl", alone or in combination with other groups, denotes a monovalent linear or branched hydrocarbon group of 2 to 6 carbon atoms, in particular from 2 to 4 carbon atoms, having one or two triple bonds. Examples of $C_{2-6}$-alkynyl include ethynyl, propynyl, prop-2-ynyl and n-butynyl. Specific groups are ethynyl and propynyl.

The term "$C_{2-6}$-alkenyl", alone or in combination with other groups, denotes a monovalent linear or branched hydrocarbon group of 2 to 6 carbon atoms, in particular from 2 to 4 carbon atoms, having one or two double bonds. Examples of $C_{2-6}$-alkenyl include ethenyl, propenyl and the like.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Particular groups are formic acid, trifluoroacetic acid and hydrochloric acid. Particular are hydrochloric acid, trifluoroacetic acid and fumaric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log$ Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately leads to the formation of the indicated and/or the desired product.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. The term "amino-protecting group" denotes groups intended to protect an amino group and includes benzyl, benzyloxycarbonyl (carbobenzyloxy, CBZ), 9-Fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups. Particular amino-protecting groups are tert-butoxycarbonyl group, a bis(dimethoxyphenyl)-phenylmethyl and dimethoxytrityl.

The term "leaving group" denotes the group with the meaning conventionally associated with it in synthetic organic chemistry, i.e., an atom or group displaceable under substitution reaction conditions. Examples of leaving groups include halogen, in particular bromo, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, and acyloxy.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments can be combined.

One embodiment of the invention is a compound of formula I,

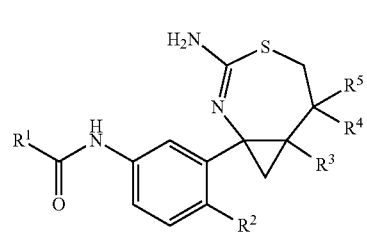

I wherein
$R^1$ is selected from the group consisting of
i) heteroaryl and
ii) heteroaryl substituted by 1-2 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkenyl, $C_{2-6}$-alkynyl and $C_{1-6}$-alkyl;

R² is selected from the group consisting of
i) hydrogen and
ii) halogen;
R³ is selected from the group consisting of
i) hydrogen and
ii) $C_{1-6}$-alkyl;
R⁴ is selected from the group consisting of
i) hydrogen,
ii) halogen, and
iii) $C_{1-6}$-alkyl;
R⁵ is selected from the group consisting of
i) hydrogen,
ii) halogen and
iii) $C_{1-6}$-alkyl;
or pharmaceutically acceptable salts thereof.

A certain embodiment of the invention provides a compound of formula Ia as described herein,

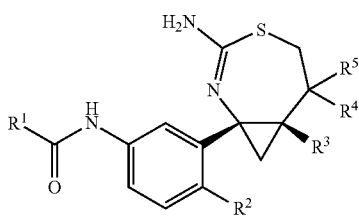

Ia wherein R¹, R², R³, R⁴, R⁵ are as defined in herein.

A certain embodiment of the invention provides a compound of formula I as described herein, wherein R¹ is heteroaryl substituted by 1-2 substituents individually selected from cyano and halogen.

A certain embodiment of the invention provides a compound of formula I as described herein, wherein R¹ is heteroaryl substituted by 1-2 substituents individually selected from cyano and chloro.

A certain embodiment of the invention provides a compound of formula I as described herein, wherein R¹ is pyridinyl substituted by 1-2 substituents individually selected from cyano and halogen.

A certain embodiment of the invention provides a compound of formula I as described herein, wherein R¹ is pyridinyl substituted by 1-2 substituents individually selected from cyano and chloro.

A certain embodiment of the invention provides a compound of formula I as described herein, wherein R¹ is heteroaryl substituted by cyano.

A certain embodiment of the invention provides a compound of formula I as described herein, wherein R¹ is 5-cyano-pyridin-2-yl.

A certain embodiment of the invention provides a compound of formula I as described herein, wherein R¹ is heteroaryl substituted by halogen.

A certain embodiment of the invention provides a compound of formula I as described herein, wherein R¹ is heteroaryl substituted by chloro.

A certain embodiment of the invention provides a compound of formula I as described herein, wherein R¹ is 5-chloro-pyridin-2-yl.

A certain embodiment of the invention provides a compound of formula I as described herein, wherein R² is halogen or hydrogen.

A certain embodiment of the invention provides a compound of formula I as described herein, wherein R² is hydrogen.

A certain embodiment of the invention provides a compound of formula I as described herein, wherein R² is halogen.

A certain embodiment of the invention provides a compound of formula I as described herein, wherein R² is F.

A certain embodiment of the invention provides a compound of formula I as described herein, wherein R² is Cl.

A certain embodiment of the invention provides a compound of formula I as described herein, wherein R³ is hydrogen.

A certain embodiment of the invention provides a compound of formula I as described herein, wherein R⁴ is hydrogen.

A certain embodiment of the invention provides a compound of formula I as described herein, wherein R⁵ is hydrogen.

A certain embodiment of the invention provides a compound of formula I as described herein, selected from the group consisting of 5-Chloro-pyridine-2-carboxylic acid [3-((1SR,7SR)-3-amino-4-thia-2-aza-bicyclo[5.1.0]oct-2-en-1-yl)-4-fluoro-phenyl]-amide, 5-Chloro-pyridine-2-carboxylic acid [3-((1S,7S)-3-amino-4-thia-2-aza-bicyclo[5.1.0]oct-2-en-1-yl)-4-fluoro-phenyl]-amide, 5-Cyano-pyridine-2-carboxylic acid [3-((1S,7S)-3-amino-4-thia-2-aza-bicyclo[5.1.0]oct-2-en-1-yl)-4-fluoro-phenyl]-amide, N-(3-((1S,7S)-3-Amino-4-thia-2-azabicyclo[5.1.0]oct-2-en-1-yl)phenyl)-5-chloropicolinamide, N-(3-((1S,7S)-3-Amino-4-thia-2-azabicyclo[5.1.0]oct-2-en-1-yl)phenyl)-5-cyanopicolinamide, N-(3-((1SR,7SR)-3-amino-4-thia-2-azabicyclo[5.1.0]oct-2-en-1-yl)-4-chlorophenyl)-5-chloropicolinamide, N-(3-((1SR,7SR)-3-Amino-4-thia-2-azabicyclo[5.1.0]oct-2-en-1-yl)phenyl)-5-chloropicolinamide, and N-(3-((1SR,7SR)-3-Amino-4-thia-2-azabicyclo[5.1.0]oct-2-en-1-yl)phenyl)-5-cyanopicolinamide, or a pharmaceutical acceptable salt thereof.

A certain embodiment of the invention provides a compound of formula I as described herein, selected from the group consisting of N-(3-((1SR,7SR)-3-Amino-4-thia-2-azabicyclo[5.1.0]oct-2-en-1-yl)phenyl)-5-chloropicolinamide, and N-(3-((1S,7S)-3-Amino-4-thia-2-azabicyclo[5.1.0]oct-2-en-1-yl)phenyl)-5-chloropicolinamide, or a pharmaceutical acceptable salt thereof.

A certain embodiment of this invention provides a process to synthesize a compound of formula I', comprising deprotecting a compound of formula A9.

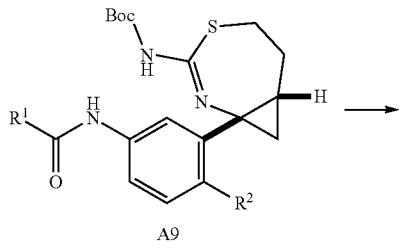

A9

-continued

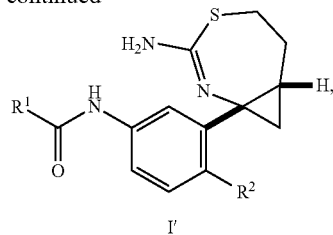

whereby $R^1$, $R^2$ and Boc have the meanings as described herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of diabetes.

A certain embodiment of the invention provides a compound of formula I as described herein for the use as therapeutically active substance for the therapeutic and/or prophylactic treatment of diabetes or type 2 diabetes.

A certain embodiment of the invention provides a compound of formula I as described herein for the use as therapeutically active substance for the therapeutic and/or prophylactic treatment of Alzheimer's disease, diabetes or type 2 diabetes.

A certain embodiment of the invention provides a compound of formula I as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides the use of a compound of formula I as described herein for the manufacture of a medicament for the therapeutic and/or prophylactic treatment of Alzheimer's disease, diabetes or type 2 diabetes.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes or type 2 diabetes.

A certain embodiment of the invention provides the use of a compound of formula I as described herein for the manufacture of a medicament for the therapeutic and/or prophylactic treatment of diabetes.

A certain embodiment of the invention provides the use of a compound of formula I as described herein for the manufacture of a medicament for the therapeutic and/or prophylactic treatment of type 2 diabetes.

A certain embodiment of the invention provides the use of a compound of formula I as described herein for the manufacture of a medicament for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of diabetes.

A certain embodiment of the invention provides a compound of formula I as described herein for the use in the therapeutic and/or prophylactic treatment of diabetes or type 2 diabetes.

A certain embodiment of the invention provides a compound of formula I as described herein for the use in the therapeutic and/or prophylactic treatment of Alzheimer's disease, diabetes or type 2 diabetes.

A certain embodiment of the invention provides a compound of formula I as described herein for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

A certain embodiment of the invention provides a method for the use in the therapeutic and/or prophylactic treatment of Alzheimer's disease, diabetes or type 2 diabetes, which method comprises administering a compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

A certain embodiment of the invention provides a method for the use in the therapeutic and/or prophylactic treatment of diabetes, which method comprises administering a compound of formula I as described herein to a human being or animal.

A certain embodiment of the invention provides a method for the use in the therapeutic and/or prophylactic treatment of type 2 diabetes, which method comprises administering a compound of formula I as described herein to a human being or animal.

A certain embodiment of the invention provides a method for the use in the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric forms, e.g. in the following tautomeric form:

Id

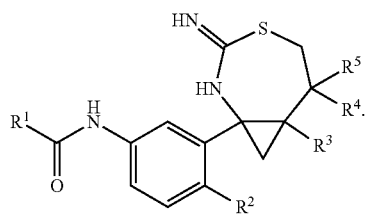

Id

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Particular example of isomers of a compound of formula I is a compound of formula Ia, wherein the residues have the meaning as described in any of the embodiments.

Ia

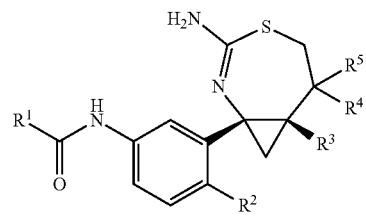

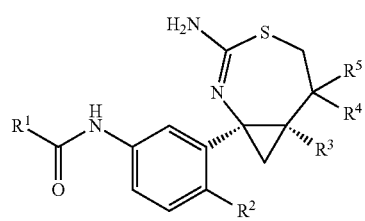

Ib

In the embodiments, where optically pure enantiomers are provided, optically pure enantiomer means that the compound contains >90% of the desired isomer by weight, in particular >95% of the desired isomer by weight, or more particular >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

Scheme A

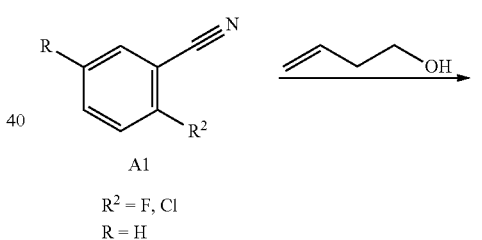

A1

$R^2$ = F, Cl
R = H

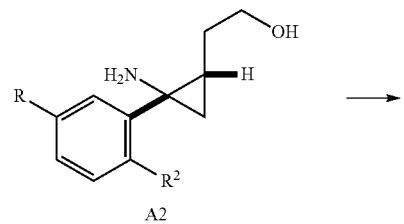

A2

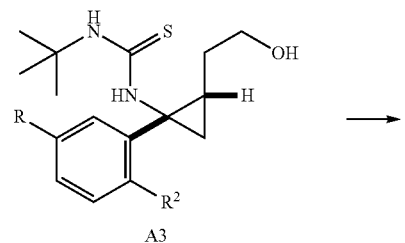

A3

-continued

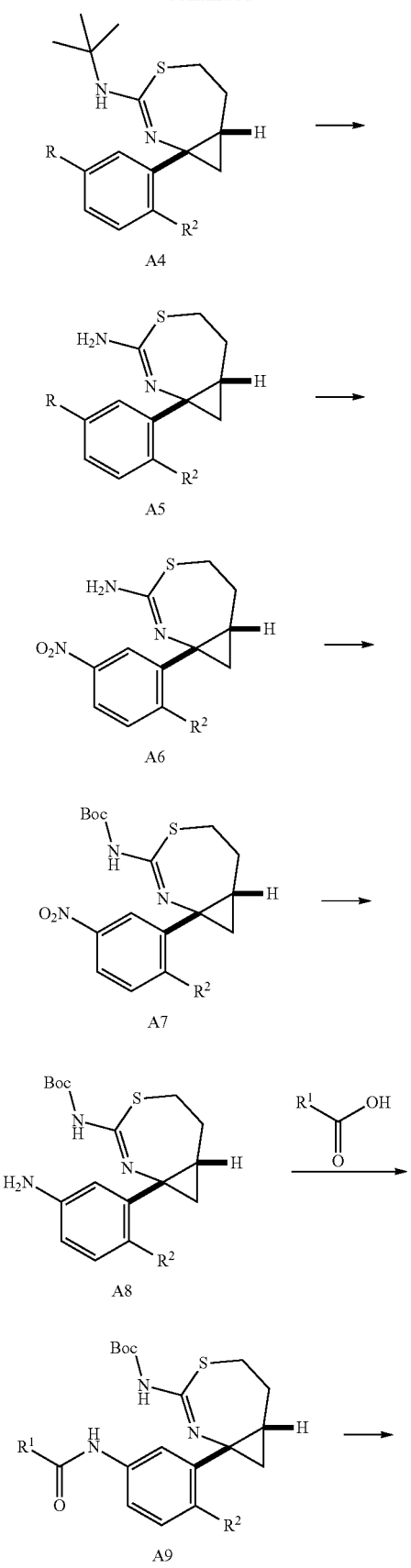

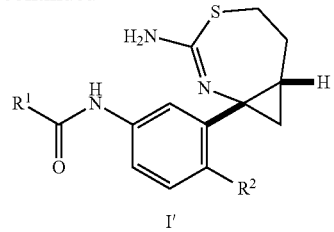

Benzonitriles of formula A1 can be reacted with 3-buten-1-ol in the presence of a titanium reagent, like e.g. tetraisopropoxytitanium or methyltriisopropoxytitanium, and an excess of a Grignard reagent, like e.g. cyclohexylmagnesium chloride or cyclopentylmagnesium chloride, in an etheral solvent, like e.g. diethyl ether or tetrahydrofuran, in a so called Kulinkovich-Szymoniak reaction as e.g. described in *Synlett* 2008, (16), 2455 to produce the cyclopropylaminoalcohols of formula A2.

Cyclopropylamines of formula A2 can be reacted with an isothiocyanate, preferably tert-butylisothiocyanate, in a solvent such as acetonitrile, tetrahydrofuran or dichloromethane at temperatures between ambient temperature or 80° C. to give the thioureas of formula A3.

Cyclization of thioureas of formula A3 to the 1,3-thiazepines of formula A4 can be achieved by treatment with a phosphine, like e.g. triphenylphosphine or tributylphosphine, and a tetrahalomethane compound such as tetrabromomethane or tetrachloromethane, in a solvent such as dichloromethane or acetonitrile at temperatures between 0° C. and ambient temperature.

Cleavage of the tert-butyl group in 1,3-thiazepines of formula A4 to the 2-amino-1,3-thiazepines of formula A5 could be achieved by reaction with a strong sulfonic acid, in particular methanesulfonic acid, in a strong carbonic acid, such as trifluoroacetic acid, at temperatures between 0 and 60° C., particular at ambient temperature.

Introduction of the nitro group in A5 to produce the nitro compound of formula A6 was best performed according to the standard procedure involving sulfuric acid and nitric acid at low temperature, particular 0° C.

Protection of the amino group of the 2-amino-1,3-thiazepines of formula A6 by introduction of the Boc-group was best performed using standard conditions, i.e. reaction with tert-butyldicarbonate in the presence of an amine base, like e.g. triethylamine or diisopropylethylamine, in an inert solvent such as dichloromethane or tetrahydrofuran at temperatures between 0° C. and ambient temperature.

The nitro group in A7 can be reduced to the aniline A8 using standard hydrogenation conditions, i.e. palladium on carbon in the presence of hydrogen and a solvent, e.g. an alcohol, particular methanol or ethanol.

The coupling of the anilines A8 and the acid was best achieved by appropriate coupling agents like carbodiimides or uronium salts, such as for example N,N'-carbonyldiimidazole (CDI), N,N'-dicyclohexylcarbodiimide (DCC), N-(3-dimethylaminopropyl)-N'-ethyl-carbodiimide-hydrochloride (EDCI), O-(benzotriazol-1-yl)-N,N,N',N'-tetramethyluronium tetrafluoroborate (TBTU) and 1-[bis(dimethylamino)methylene]-1H-1,2,3-triazolo[4,5-b]pyridinium-3-oxide hexafluorophosphate (HATU) under basic conditions, i.e. in the presence of a base, in particular an alkylamine such as diisopropylethylamine (DIEA) or triethylamine (TEA), or a tertiary amine such as N-methylmorpholine or 4-(dimethylamino)-pyridine. The reaction is carried out in a suitable solvent such as for example N,N-dimethylformamide (DMF), dimethylacetamide (DMAc) or dichloromethane (DCM), at temperatures between 0° C. and ambient temperature, to give the amides A9.

Deprotection of the tert-butyl carbamate A9 to the final compound I' can be accomplished by a strong carbonic acid, e.g. trifluoroacetic acid in a halogenated solvent, e.g dichloromethane at temperatures between 0° C. and ambient temperature.

Intermediates of formula A2 can alternatively be prepared as illustrated in the following Scheme B.

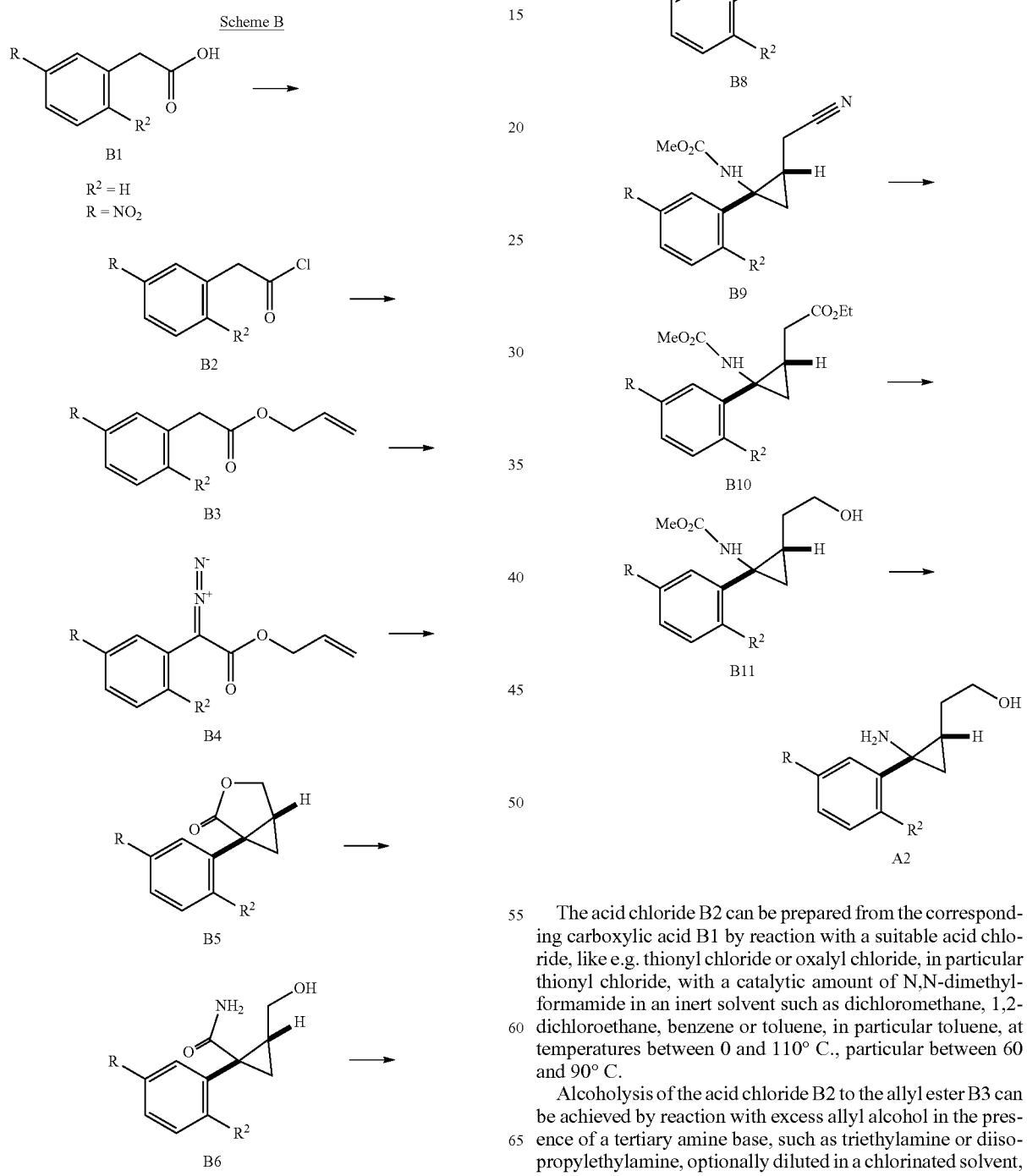

The acid chloride B2 can be prepared from the corresponding carboxylic acid B1 by reaction with a suitable acid chloride, like e.g. thionyl chloride or oxalyl chloride, in particular thionyl chloride, with a catalytic amount of N,N-dimethylformamide in an inert solvent such as dichloromethane, 1,2-dichloroethane, benzene or toluene, in particular toluene, at temperatures between 0 and 110° C., particular between 60 and 90° C.

Alcoholysis of the acid chloride B2 to the allyl ester B3 can be achieved by reaction with excess allyl alcohol in the presence of a tertiary amine base, such as triethylamine or diisopropylethylamine, optionally diluted in a chlorinated solvent, such as dichloromethane or 1,2-dichloroethane, in particular dichloromethane, at temperatures between −20 and 23° C., particular between 0 and 23° C.

Using the Regitz diazotransfer reaction the allyl ester B3 can be converted into the allyl α-diazoester B4 by treatment with a sulfonyl azide, such as 4-toluenesulfonyl azide, methanesulfonyl azide, 4-dodecylbenzenesulfonyl azide or 4-acetamidobenzenesulfonyl azide, in particular 4-acetamidobenzenesulfonyl azide, in the presence of an amine base such as 1,8-diazabicyclo[5.4.0]undec-7-ene (DBU) or 1,5-diazabicyclo[4.3.0]non-5-ene (DBN), in particular DBU, in an etheral solvent, such as diethyl ether, 1,2-dimethoxyethane or THF, in particular THF, at temperatures between 0 and 23° C., in particular 23° C.

The allyl α-diazoester B4 can be cyclized to the lactone B5 under extrusion of dinitrogen by treatment with a catalytic amount of a transition metal complex, such as copper(I) or copper(II) complexes, like e.g. ((4S,4'S)-4,4',5,5'-tetrahydro-2,2'-methylene-4,4'-dibenzyl-bisoxazole)copper(I) trifluoromethanesulfonate, copper(II)(acetylacetonate)$_2$ or bis(N-tert-butylsalicylaldiminato)copper(II), cobalt(II) complexes, like e.g. (1,3-bis((6aR,7aS)-7,7-dimethyl-6,6a,7,7a-tetrahydro-5H-cyclopropa(h)quinolin-2-imino)-4,5,6,7-tetraphenylisoindol-1-yl)cobalt(II) acetate, ruthenium(I) or ruthenium(II) complexes, like e.g. Ru((1R,2R)—N,N'-bis(2-bromosalicylidene)-1,2-cyclohexanediamine)(PPh$_3$)$_2$, rhodium(II) complexes, like e.g. rhodium (II) acetate dimer, rhodium (II) octanoate dimer, dirhodium(II) tetrakis((R)—N-((4-dodecyl)phenylsulfonyl)prolinate), dirhodium(II) tetrakis(4'-fluorobenzyl 2-azetidinone-4(S)-carboxylate), dirhodium(II) tetrakis(methyl azetidin-2-one-4(S)-carboxylate), in particular rhodium(II) complexes, more particular rhodium(II) carboxylate dimers, in an inert solvent such as dichloromethane, 1,2-dichloroethane, benzene or toluene, in particular dichloromethane, at temperatures between 0 and 110° C., in particular between 23 and 40° C.

Examples for a similar sequence as described here from acid B1 to lactone B5 and the potential of using a chiral ligand in the rhodium(II) complexes for the generation of an enantiomerically enriched or pure compound has been described several times by Doyle, M. P. et al. in *Org. Lett.* 2000, 2(8), 1145-1147, *Adv. Synth. Catal.* 2001, 343(1), 112-117 and in *Adv. Synth. Catal.* 2001, 343(3), 299-302.

Ring opening of the lactone B5 to the amide B6 can be accomplished by reaction with ammonia in an alcoholic solvent such as methanol or ethanol, in particular methanol, in a sealed vessel at temperatures between 23 and 100° C., in particular at 50 to 60° C.

The Hoffmann rearrangement of the amide B6 to the cyclic carbamate B7 can be achieved by treatment with a hypochlorite or hypobromite solution, in particular hypobromite, in a solvent mixture consisting of water, an alcohol, such as methanol or ethanol, in particular methanol, and an ether, such as diethyl ether, 1,2-dimethoxyethane, 1,4-dioxane or THF, in particular THF, at temperatures between −20 and 23° C., in particular at 23° C. During this reaction the intermediate isocyanate either reacts with the alcoholic solvent methanol to the ring openened carbamate B7 or cyclizes with the hydroxy group to the corresponding cyclic carbamate (not shown). The cyclic carbamate can be saponified to the amino alcohol by reaction with an aqueous hydroxide solution, like e.g. lithium hydroxide, sodium hydroxide or potassium hydroxide, in particular lithium hydroxide, in presence of an alcohol such as methanol, ethanol, n-propanol or isopropanol, in particular ethanol, at temperatures between 23 and 120° C., in particular between 80 and 100° C. Afterwards the amino alcohol can be reacted with a suitable alkyl chloroformate like e.g. methyl chloroformate in the presence of an amine base like e.g. triethylamine or diisopropylethylamine in an inert solvent like e.g. dichloromethane at temperatures between 0 and 23° C. to produce the carbamate B7.

The alcohol B7 could be converted into the sulfonate B8 by standard condition using an organic sulfonyl chloride such as methanesulfonyl chloride in the presence of an amine base such as triethylamine of diisopropylethylamine in a chlorinated solvent such as dichloromethane at temperatures between 0 and 23° C., in particular 0° C.

The sulfonate B8 could be transformed into the nitrile B9 by reaction with an alkali cyanide salt, like e.g. potassium cyanide or sodium cyanide, in a polar aprotic solvent, like e.g. N,N-dimethylformamide, N,N-dimethylacetamide or dimethylsulfoxide, at temperatures between 23 and 80° C.

The nitrile B9 could be alcoholized to the ester of formula B10 by treatment with thionyl chloride in ethanol at temperatures between 23 and 80° C., in particular 80° C.

The ester of formula B10 can be reduced to the alcohol B11 by the reduction of the ethylester with an alkali hydride, in particular lithium borohydride or sodium borohydride in a solvent such as an ether, e.g. diethyl ether or more in particular THF.

The carbamate B11 can be saponified to the amino alcohol A2 by reaction with an aqueous hydroxide solution, like e.g. lithium hydroxide, sodium hydroxide or potassium hydroxide, in particular lithium hydroxide, in presence of an alcohol such as methanol, ethanol, n-propanol or isopropanol, in particular ethanol, at temperatures between 23 and 120° C., in particular between 80 and 100° C.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of formula I in this invention can be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 and/or BACE2 activity. The compounds were investigated in accordance with the test given hereinafter.

Cellular Aβ-Lowering Assay:

a) Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/$H_2O_2$ in citric acid buffer. After stopping the reaction with one volume 1 N $H_2SO_4$ the reaction was measured in an ELISA reader at 450 nm wavelength. The concentrations of Aβ in the culture supernatants were calculated from a standard curve obtained with known amounts of pure Aβ peptide.

b) Alternatively, the Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in 1/3 volume of culture medium (final DMSO concentration was kept at 1% v/v). After 18-20 hrs incubation at 37° C. and 5% $CO_2$ in a humidified incubator, the culture supernatants were harvested for the determination of Aβ 40 concentrations using Perkin-Elmer Human Amyloid beta 1-40 (high specificity) Kit (Cat# AL275C).

In a Perkin-Elmer White Optiplate-384 (Cat#6007290), 2 ul culture supernatants were combined with 2 μl of a 10× AlphaLISA Anti-hAβ Acceptor beads+Biotinylated Antibody Anti-Aβ 1-40 Mix (50 μg/mL/5 nM). After 1 hour room temperature incubation, 16 μl of a 1.25× preparation of Streptavidin (SA) Donor beads (25 μg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The IC50 values were calculated using the Excel XLfit software.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+ Glutamax (Invitrogen) Penicillin/Streptomycin, 10% Fetal bovine serum, 100 mM pyruvate, 5 mM beta-mercaptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

TABLE 1

$IC_{50}$ values of selected examples

| Exam. | BACE1 $IC_{50}$ [μM] | BACE2 $IC_{50}$ [μM] |
|---|---|---|
| 1 | $0.012^a$ | 0.011 |
| 2 | $0.026^a$ | 0.002 |
| 3 | $0.060^b$ | 0.005 |
| 4 | — | 0.690 |
| 5 | $0.050^b$ | 0.002 |
| 6 | $0.052^b$ | 0.001 |
| 7 | $0.005^a$ | 0.002 |
| 8 | $0.031^a$ | 0.001 |

Pharmaceutical Compositions

The compounds of formula I and their pharmaceutically acceptable salts can be used as therapeutically active substances, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injectable solutions.

The compounds of formula I and the pharmaceutically acceptable salts thereof can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, in particular 1-100 mg, of a compound of formula I. Examples of compositions according to the invention are:

Example A

Tablets of the following composition are manufactured in the usual manner:

TABLE 2 possible tablet composition

|  | mg/tablet | | | |
| --- | --- | --- | --- | --- |
| ingredient | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

|  | mg/capsule | | | |
| --- | --- | --- | --- | --- |
| ingredient | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
| --- | --- |
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
| --- | --- |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
| --- | --- |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7

| possible injection solution composition | |
| --- | --- |
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8

| possible sachet composition | |
| --- | --- |
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

General

NMR: $^1$H NMR spectra were recorded on a Bruker AC-300 spectrometer at 25° C. with TMS (tetramethylsilane) or residual $^1$H of the given deuterated solvents as internal standards. MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

Intermediate A1a: 2-((1SR,2SR)-2-Amino-2-(2-fluorophenyl)cyclopropyl)ethanol

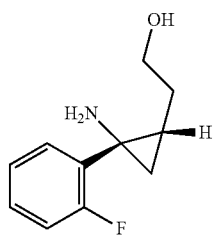 [SMILES: N[C@@]1(c2ccccc2F)C[C@H]1CCO]

To a solution of tetraisopropoxytitanium (45.3 g, 47.2 ml, 159 mmol, Eq: 2) and diethyl ether (280 ml) was added dropwise at −70° C. cyclohexylmagnesium chloride (2 M in diethyl ether; 199 ml, 399 mmol, Eq: 5). After stiffing for 20 min at −70° C. a solution of 2-fluorobenzonitrile (19.3 g, 16.9 ml, 159 mmol, Eq: 2) and but-3-en-1-ol (5.75 g, 6.85 ml, 79.7 mmol, Eq: 1.00) in diethyl ether (140 ml) was added via a dropping funnel quite quickly (rise of temperature to −35° C.). The cooling bath was removed and the reaction mixture was stirred at 23° C. for 20 hours. Poured into ice cold 1 M NaOH (400 ml) followed by the extraction with tert-butyl methyl ether. The organic layers were washed with water and brine, dried over $Na_2SO_4$, filtered and evaporated to give a yellow oil (33 g) which was chromatographed on 250 g $SiO_2$ with ethyl acetate to give the 2-((1SR,2SR)-2-amino-2-(2-fluorophenyl)cyclopropyl)ethanol (3.28 g, 16.8 mmol, 21.1% yield) as a yellow oil. MS (ISP): m/z=196.2 [(M+H)$^+$].

Intermediate A2b: 2-((1SR,2SR)-2-Amino-2-(2-chlorophenyl)cyclopropyl)ethanol

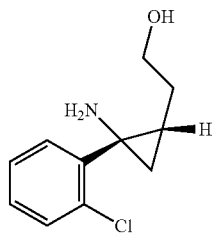 [SMILES: N[C@@]1(c2ccccc2Cl)C[C@H]1CCO]

Prepared in an analogous manner as described for intermediate A2a from 2-chlorobenzonitrile (22.0 g, 160 mmol) to give the 2-((1SR,2SR)-2-amino-2-(2-chlorophenyl)cyclopropyl)ethanol (3.16 g, 11.9 mmol, 14.9% yield) as a yellow oil (ca. 80% purity). MS (ISP): m/z=212.2 [(M+H)$^+$] and 214.2 [(M+2+H)$^+$].

Intermediate A2c: Methyl (1SR,2SR)-2-(2-hydroxyethyl)-1-(3-nitrophenyl)cyclopropylcarbamate

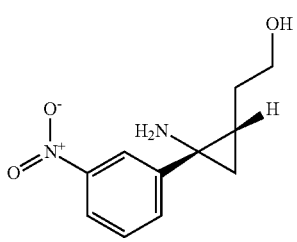 [SMILES: N[C@@]1(c2cccc([N+](=O)[O-])c2)C[C@H]1CCO]

To a suspension of methyl (1SR,2SR)-2-(2-hydroxyethyl)-1-(3-nitrophenyl)cyclopropylcarbamate (intermediate B11a) (1.84 g, 6.56 mmol, Eq: 1.00) in 1,4-dioxane (20 ml) and water (20 ml) was added lithium hydroxide (1.57 g, 65.6 mmol, Eq: 10) and the reaction mixture was stirred at 100° C. for 24 hours. To the cooled reaction mixture was added 25% HCl (pH=1). After stiffing for 10 min at 23° C., conc NaOH was added until pH=10. Extraction with dichloromethane, drying over $Na_2SO_4$, filtration and evaporation of the solvent in vacuum left a light brown solid. Crystallization with dichloromethane/cyclohexane gives the 2-((1SR,2SR)-2-amino-2-(3-nitrophenyl)cyclopropyl)ethanol (1.29 g, 5.8 mmol, 88.4% yield) as a light brown solid. MS (ISP): m/z=223.2 [(M+H)$^+$].

Intermediate A3a: 1-tert-Butyl-3-[(1SR,2SR)-1-(2-fluoro-phenyl)-2-(2-hydroxy-ethyl)-cyclopropyl]-thiourea

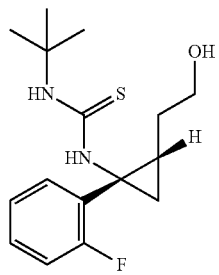 [SMILES: CC(C)(C)NC(=S)N[C@@]1(c2ccccc2F)C[C@H]1CCO]

Prepared in an analogous manner as described for intermediate A3c from 2-((1SR,2SR)-2-amino-2-(2-fluorophenyl)cyclopropyl)ethanol (intermediate A2a) (2.65 g, 13.6 mmol) to give the 1-tert-butyl-3-((1SR,2SR)-1-(2-fluorophenyl)-2-(2-hydroxyethyl)cyclopropyl)thiourea (2.05 g, 6.6 mmol, 48.7% yield) as a light brown solid. MS (ISP): m/z=311.2 [(M+H)$^+$].

Intermediate A3b: 1-tert-Butyl-3-[(1SR,2SR)-1-(2-chloro-phenyl)-2-(2-hydroxy-ethyl)-cyclopropyl]-thiourea

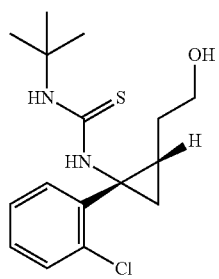 [SMILES: CC(C)(C)NC(=S)N[C@@]1(c2ccccc2Cl)C[C@H]1CCO]

Prepared in an analogous manner as described for intermediate A3c from 2-((1SR,2SR)-2-amino-2-(2-chlorophenyl)cyclopropyl)ethanol (intermediate A2b) (3.15 g, 11.9 mmol) to give the 1-tert-butyl-3-((1SR,2SR)-1-(2-chlorophenyl)-2-(2-hydroxyethyl)cyclopropyl)thiourea (1.87 g, 5.72 mmol, 48.1% yield) as a yellow gum. MS (ISP): m/z=327.2 [(M+H)$^+$] and 329.1 [(M+2+H)$^+$].

Intermediate A3c: 1-tert-Butyl-3-((1SR,2SR)-2-(2-hydroxyethyl)-1-(3-nitrophenyl)cyclopropyl)thiourea

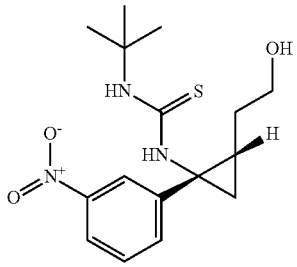 [SMILES: CC(C)(C)NC(=S)N[C@@]1(c2cccc([N+](=O)[O-])c2)C[C@H]1CCO]

To a solution of 2-((1SR,2SR)-2-amino-2-(3-nitrophenyl)cyclopropyl)ethanol (intermediate A2c) (1.44 g, 6.48 mmol, Eq: 1.00) in dry acetonitrile (30 ml) was added at 23° C. tert-butyl isothiocyanate (1.12 g, 1.23 ml, 9.72 mmol, Eq: 1.5) and the mixture was stirred at 80° C. for 36 h. Evaporated to dryness and chromatography. The residue was chromatographed on 50 g $SiO_2$ with 0-50% ethyl acetate in dichloromethane to give the 1-tert-butyl-3-((1SR,2SR)-2-(2-hydroxyethyl)-1-(3-nitrophenyl)cyclopropyl)thiourea (1.47 g, 4.36 mmol, 67.2% yield) as a light brown solid. MS (ISP): m/z=338.4 [(M+H)$^+$].

Intermediate A4a: (1SR,7SR)—N-tert-butyl-1-(2-fluorophenyl)-4-thia-2-azabicyclo[5.1.0]oct-2-en-3-amine

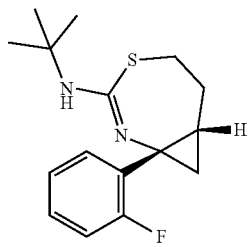 [SMILES: CC(C)(C)NC1=N[C@@]2(c3ccccc3F)C[C@H]2CCS1]

Prepared in an analogous manner as described for intermediate A4c from 1-tert-butyl-3-((1SR,2SR)-1-(2-fluorophenyl)-2-(2-hydroxyethyl)cyclopropyl)thiourea (intermediate A3a) (2 g, 6.44 mmol) to give the (1SR,7SR)—N-tert-butyl-1-(2-fluorophenyl)-4-thia-2-azabicyclo[5.1.0]oct-2-en-3-amine (1.90 g, 6.5 mmol, 101% yield; 90% purity) as a light brown oil. MS (ISP): m/z=293.1 [(M+H)$^+$].

Intermediate A4b: (1SR,7SR)—N-tert-butyl-1-(2-chlorophenyl)-4-thia-2-azabicyclo[5.1.0]oct-2-en-3-amine

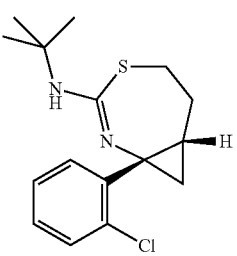 [SMILES: CC(C)(C)NC1=N[C@@]2(c3ccccc3Cl)C[C@H]2CCS1]

Prepared in an analogous manner as described for intermediate A4c from 1-tert-butyl-3-((1SR,2SR)-1-(2-chlorophenyl)-2-(2-hydroxyethyl)cyclopropyl)thiourea (intermediate A3b) (1.87 g, 5.72 mmol) to give the (1SR,7SR)—N-tert-butyl-1-(2-chlorophenyl)-4-thia-2-azabicyclo[5.1.0]oct-2-en-3-amine (1.75 g, 5.1 mmol, 89.1% yield; 90% purity) as a light brown semisolid. MS (ISP): m/z=309.2 [(M+H)$^+$] and 311.1 [(M+2+H)$^+$].

Intermediate A4c: (1SR,7SR)—N-tert-Butyl-1-(3-nitrophenyl)-4-thia-2-azabicyclo[5.1.0]oct-2-en-3-amine

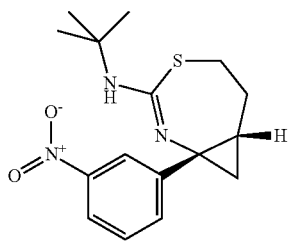 [SMILES: CC(C)(C)NC1=N[C@@]2(c3cccc([N+](=O)[O-])c3)C[C@H]2CCS1]

tert-Butyl-3-((1SR,2SR)-2-(2-hydroxyethyl)-1-(3-nitrophenyl)cyclopropyl)thiourea (intermediate A3c) (1.47 g, 4.36 mmol, Eq: 1.00) was dissolved in dichloromethane (50 ml), then at 0° C. triphenylphosphine (2.06 g, 7.84 mmol, Eq: 1.8) and carbon tetrabromide (2.6 g, 7.84 mmol, Eq: 1.8) were added. The reaction mixture was stirred at 0° C. for 2 hours. To the reaction mixture was added 60 ml of sat. NaHCO$_3$ solution and stirred for 15 min. Then more dichloromethane, water and brine were added and extracted. The organic layer was separated and washed with brine and then dried over Na$_2$SO$_4$. Removal of the solvent in vacuum left a brown oil which was chromatographed on 50 g SiO$_2$ with 0-50% ethyl acetate in heptane to give the (1SR,7SR)—N-tert-butyl-1-(3-nitrophenyl)-4-thia-2-azabicyclo[5.1.0]oct-2-en-3-amine (995 mg, 3.12 mmol, 71.5% yield) as a light yellow oil. MS (ISP): m/z=320.1 [(M+H)$^+$].

Intermediate A5a: (1SR,7SR)-1-(2-Fluoro-phenyl)-4-thia-2-aza-bicyclo[5.1.0]oct-2-en-3-ylamine

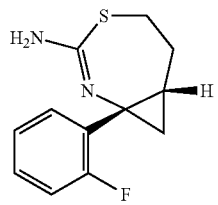 [SMILES: NC1=N[C@@]2(c3ccccc3F)C[C@H]2CCS1]

Prepared in an analogous manner as described for intermediate A6c from (1SR,7SR)—N-tert-butyl-1-(2-fluorophenyl)-4-thia-2-azabicyclo[5.1.0]oct-2-en-3-amine (intermediate A4a) (1.9 g, 6.5 mmol) to give the (1SR,7SR)-1-(2-fluorophenyl)-4-thia-2-azabicyclo[5.1.0]oct-2-en-3-amine (1.22 g, 5.16 mmol, 79.5% yield) as a light brown solid. MS (ISP): m/z=237.2 [(M+H)$^+$].

Intermediate A5b: (1SR,7SR)-1-(2-Chloro-phenyl)-4-thia-2-aza-bicyclo[5.1.0]oct-2-en-3-ylamine

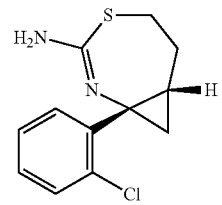

Prepared in an analogous manner as described for intermediate A6c from (1SR,7SR)—N-tert-butyl-1-(2-chlorophenyl)-4-thia-2-azabicyclo[5.1.0]oct-2-en-3-amine (intermediate A4b) (1.75 g, 5.1 mmol) to give the (1SR,7SR)-1-(2-chlorophenyl)-4-thia-2-azabicyclo[5.1.0]oct-2-en-3-amine (843 mg, 3.34 mmol, 65.4% yield) as a light yellow solid. MS (ISP): m/z=253.1 [(M+H)$^+$] and 255.2 [(M+2+H)$^+$].

Intermediate A6a: (1SR,7SR)-1-(2-Fluoro-5-nitrophenyl)-4-thia-2-azabicyclo[5.1.0]oct-2-en-3-amine

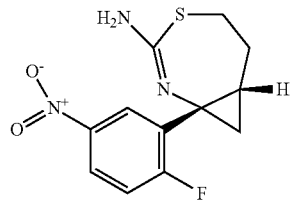 [SMILES: NC1=N[C@@]2(c3cc([N+](=O)[O-])ccc3F)C[C@H]2CCS1]

(1SR,7SR)-1-(2-Fluorophenyl)-4-thia-2-azabicyclo[5.1.0]oct-2-en-3-amine (intermediate A5a) (1.22 g, 5.16 mmol, Eq: 1.00) was dissolved in conc. sulfuric acid (20.3 g, 11.0 ml, 207 mmol, Eq: 40), then at 0° C. fuming nitric acid (488 mg, 321 µl, 7.74 mmol, Eq: 1.5) was added dropwise with an Eppendorf pipette. The light brown solution was stirred at 0° C. for 2 hours. The reaction mixture was poured on ice and basified with conc NaOH (pH=10) followed by the extraction with dichloromethane. The organic layer was separated, dried over Na$_2$SO$_4$, filtered and evaporated to dryness to give the (1SR,7SR)-1-(2-fluoro-5-nitrophenyl)-4-thia-2-azabicyclo[5.1.0]oct-2-en-3-amine (995 mg, 3.54 mmol, 68.5% yield). as a yellow solid. The crude product was used in the next step without further purification. MS (ISP): m/z=237.2 [(M+H)$^+$].

Intermediate A6b: (1SR,7SR)-1-(2-Chloro-5-nitrophenyl)-4-thia-2-azabicyclo[5.1.0]oct-2-en-3-amine

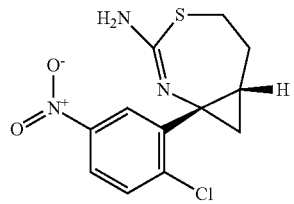 [SMILES: NC1=N[C@@]2(c3cc([N+](=O)[O-])ccc3Cl)C[C@H]2CCS1]

Prepared in an analogous manner as described for intermediate A6a from (1SR,7SR)-1-(2-chlorophenyl)-4-thia-2-azabicyclo[5.1.0]oct-2-en-3-amine (intermediate A5b) (650 mg, 2.57 mmol) to give the (1SR,7SR)-1-(2-chloro-5-nitrophenyl)-4-thia-2-azabicyclo[5.1.0]oct-2-en-3-amine (715 mg, 2.02 mmol, 78.4% yield) as a light brown solid. MS (ISP): m/z=298.0 [(M+H)$^+$] and 300.0 [(M+2+H)$^+$].

Intermediate A6c: (1SR,7SR)-1-(3-Nitrophenyl)-4-thia-2-azabicyclo[5.1.0]oct-2-en-3-amine

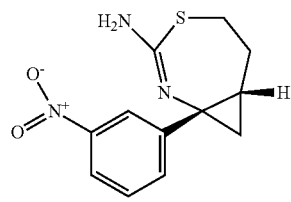 [SMILES: NC1=N[C@@]2(c3cccc([N+](=O)[O-])c3)C[C@H]2CCS1]

To a solution of (1SR,7SR)—N-tert-butyl-1-(3-nitrophenyl)-4-thia-2-azabicyclo[5.1.0]oct-2-en-3-amine (intermediate A4c) (990 mg, 3.1 mmol, Eq: 1.00) in trifluoroacetic acid (25.4 g, 17.2 ml, 223 mmol, Eq: 72) was added methanesulfonic acid (2.98 g, 2.01 ml, 31.0 mmol, Eq: 10) and the mixture was stirred at 23° C. for 20 hours. The light brown solution was poured cautiously into sat NaHCO$_3$ solution, extracted with ethyl acetate, washed the organic layer with brine and dried over Na$_2$SO$_4$. Removal of the solvent in vacuum left a light brown oil (910 mg, ca. 90% purity; 100%). The crude product either chromatographed on amine-coated silica gel using n-heptane and ethyl acetate or was used in the next step without further purification. MS (ISP): m/z=264.1 [(M+H)$^+$].

Intermediate rac-A7a: tert-Butyl (1SR,7SR)-1-(2-fluoro-5-nitrophenyl)-4-thia-2-azabicyclo[5.1.0]oct-2-en-3-ylcarbamate

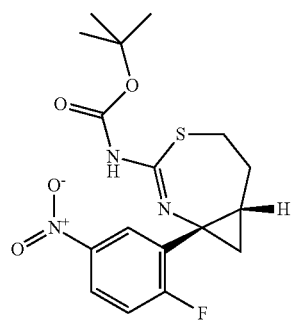

(1SR,7SR)-1-(2-Fluoro-5-nitrophenyl)-4-thia-2-azabicyclo[5.1.0]oct-2-en-3-amine (intermediate A6a) (990 mg, 3.52 mmol, Eq: 1.00) was dissolved in THF (50 ml) and triethylamine (926 mg, 1.28 ml, 9.15 mmol, Eq: 2.6) and di-tert-butyl dicarbonate (Boc$_2$O) (1.31 g, 5.98 mmol, Eq: 1.7) were added. The brown solution was stirred at 23° C. for 16 hours. Water and ethyl acetate were added to the reaction solution, and the organic layer was separated. The organic layer was washed with brine, dried over Na$_2$SO$_4$, filtered and evaporated to give a yellow oil (2.5 g; 186%), which was chromatographed on 20 g SiO$_2$ with 0-50% ethyl acetate in heptane to give the tert-butyl (1SR,7SR)-1-(2-fluoro-5-nitrophenyl)-4-thia-2-azabicyclo[5.1.0]oct-2-en-3-ylcarbamate (710 mg, 1.86 mmol, 52.9% yield) as a light yellow foam. MS (ISP): m/z=382.2 [(M+H)$^+$].

Intermediate (−)-A7a: tert-Butyl (1S,7S)-1-(2-fluoro-5-nitrophenyl)-4-thia-2-azabicyclo[5.1.0]oct-2-en-3-ylcarbamate

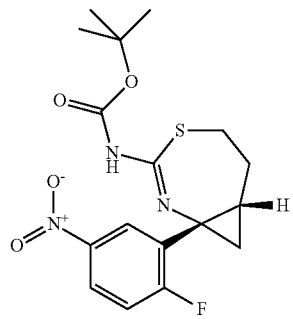 [SMILES: CC(C)(C)OC(=O)NC1=N[C@@]2(c3cc([N+](=O)[O-])ccc3F)C[C@H]2CCS1]

Chiral separation of tert-butyl (1SR,7SR)-1-(2-fluoro-5-nitrophenyl)-4-thia-2-azabicyclo[5.1.0]oct-2-en-3-ylcarbamate (intermediate rac-A7a) on a Chiralpak AD column with n-heptane/isopropanol 90:10 as eluent (flow: 35 ml/min, 20 bar pressure; UV detection: 220 nm) gave the slower eluting enantiomer tert-butyl (1S,7S)-1-(2-fluoro-5-nitrophenyl)-4-thia-2-azabicyclo[5.1.0]oct-2-en-3-ylcarbamate as a white foam showing negative (−) optical rotation (100% ee). Optical rotation: −377.9°; 589 nm, c=0.322; CHCl$_3$; 20° C.

Intermediate (+)-A7a: tert-Butyl (1R,7R)-1-(2-fluoro-5-nitrophenyl)-4-thia-2-azabicyclo[5.1.0]oct-2-en-3-ylcarbamate

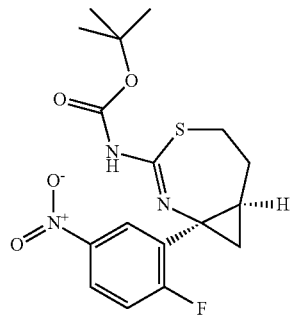

Chiral separation of tert-butyl (1SR,7SR)-1-(2-fluoro-5-nitrophenyl)-4-thia-2-azabicyclo[5.1.0]oct-2-en-3-ylcarbamate (intermediate rac-A7a) on a Chiralpak AD column with n-heptane/isopropanol 90:10 as eluent (flow: 35 ml/min, 20 bar pressure; UV detection: 220 nm) gave the faster eluting enantiomer tert-butyl (1R,7R)-1-(2-fluoro-5-nitrophenyl)-4-thia-2-azabicyclo[5.1.0]oct-2-en-3-ylcarbamate as a white foam showing positive (+) optical rotation (100% ee). Optical rotation: +376.1°; 589 nm, c=0.183; CHCl$_3$; 20° C.

Intermediate rac-A7b: tert-Butyl (1SR,7SR)-1-(2-chloro-5-nitrophenyl)-4-thia-2-azabicyclo[5.1.0]oct-2-en-3-ylcarbamate

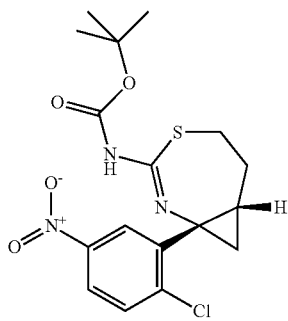 [SMILES: CC(C)(C)OC(=O)NC1=N[C@@]2(c3cc([N+](=O)[O-])ccc3F)C[C@H]2CCS1]

Prepared in an analogous manner as described for intermediate rac-A7a from (1SR,7SR)-1-(2-chloro-5-nitrophenyl)-4-thia-2-azabicyclo[5.1.0]oct-2-en-3-amine (intermediate A6b) (712 mg, 2.01 mmol, Eq: 1.00) to give the tert-butyl (1SR,7SR)-1-(2-chloro-5-nitrophenyl)-4-thia-2-azabicyclo[5.1.0]oct-2-en-3-ylcarbamate (605 mg, 1.52 mmol, 75.7% yield) as a light yellow foam. MS (ISP): m/z=398.0 [(M+H)$^+$] and 400.1 [(M+2+H)$^+$].

Intermediate rac-A7c: tert-Butyl (1SR,7SR)-1-(3-nitrophenyl)-4-thia-2-azabicyclo[5.1.0]oct-2-en-3-ylcarbamate

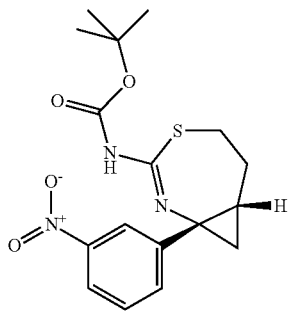 [SMILES: CC(C)(C)OC(=O)NC1=N[C@@]2(c3cccc([N+](=O)[O-])c3)C[C@H]2CCS1]

Prepared in an analogous manner as described for intermediate rac-A7a from (1SR,7SR)-1-(3-nitrophenyl)-4-thia-2-azabicyclo[5.1.0]oct-2-en-3-amine (intermediate A6c) (910 mg, 3.11 mmol, Eq: 1.00) to give the tert-butyl (1SR,7SR)-1-(3-nitrophenyl)-4-thia-2-azabicyclo[5.1.0]oct-2-en-3-ylcarbamate (755 mg, 2.08 mmol, 66.8% yield) as a yellow foam. MS (ISP): m/z=308.1 [(M+H)$^+$].

Intermediate (−)-A7c: tert-Butyl (1S,7S)-1-(3-nitrophenyl)-4-thia-2-azabicyclo[5.1.0]oct-2-en-3-ylcarbamate

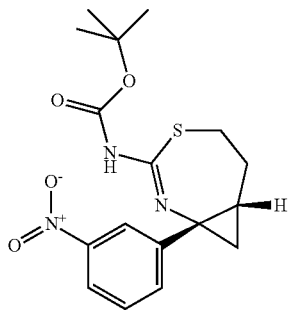 [SMILES: CC(C)(C)OC(=O)NC1=N[C@@]2(c3cccc([N+](=O)[O-])c3)C[C@H]2CCS1]

Chiral separation of tert-butyl (1SR,7SR)-1-(3-nitrophenyl)-4-thia-2-azabicyclo[5.1.0]oct-2-en-3-ylcarbamate (intermediate rac-A7c) on a Chiralpak AD column with n-heptane/isopropanol 85:15 as eluent (flow: 35 ml/min, 20 bar pressure; UV detection: 220 nm) gave the slower eluting enantiomer tert-butyl (1S,7S)-1-(3-nitrophenyl)-4-thia-2-azabicyclo[5.1.0]oct-2-en-3-ylcarbamate as a white foam showing negative (−) optical rotation (89.2% ee).

Intermediate (+)-A7c: tert-Butyl (1R,7R)-1-(3-nitrophenyl)-4-thia-2-azabicyclo[5.1.0]oct-2-en-3-ylcarbamate

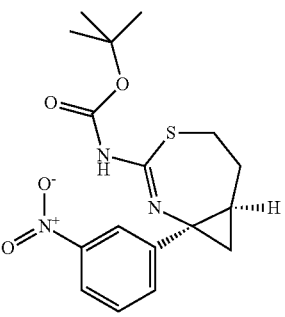 [SMILES: CC(C)(C)OC(=O)NC1=N[C@]2(c3cccc([N+](=O)[O-])c3)C[C@@H]2CCS1]

Chiral separation of tert-butyl (1SR,7SR)-1-(3-nitrophenyl)-4-thia-2-azabicyclo[5.1.0]oct-2-en-3-ylcarbamate (intermediate rac-A7c) on a Chiralpak AD column with n-heptane/isopropanol 85:15 as eluent (flow: 35 ml/min, 20 bar pressure; UV detection: 220 nm) gave the faster eluting enantiomer tert-butyl (1R,7R)-1-(3-nitrophenyl)-4-thia-2-azabicyclo[5.1.0]oct-2-en-3-ylcarbamate as a white foam showing positive (+) optical rotation (100% ee).

Intermediate rac-A8a: tert-Butyl (1SR,7SR)-1-(5-amino-2-fluorophenyl)-4-thia-2-azabicyclo[5.1.0]oct-2-en-3-ylcarbamate

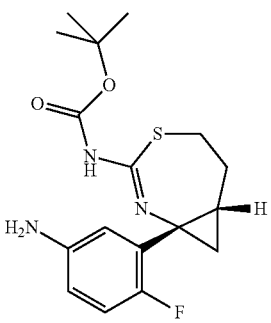 [SMILES: CC(C)(C)OC(=O)NC1=N[C@@]2(c3cc(N)ccc3F)C[C@H]2CCS1]

tert-Butyl (1SR,7SR)-1-(2-fluoro-5-nitrophenyl)-4-thia-2-azabicyclo[5.1.0]oct-2-en-3-ylcarbamate (intermediate rac-A7a) (68 mg; 0.18 mmol) was dissolved in 20 ml methanol under argon and 10% palladium on carbon (Pd/C) (28 mg, 15 mol %) was added. The atmosphere of the reaction system was replaced with hydrogen, followed by stiffing at 23° C. for 3 hours. More 10% Pd/C (67 mg) was added and stiffing was continued under hydrogen atmosphere for 20 hours. The reaction mixture was filtered and evaporated to give the tert-butyl (1SR,7SR)-1-(5-amino-2-fluorophenyl)-4-thia-2-azabicyclo[5.1.0]oct-2-en-3-ylcarbamate (53 mg; 85%) as a grey foam which was used in the next step without further purification. MS (ISP): m/z=352.3 [(M+H)$^+$].

Intermediate (−)-A8a: tert-Butyl (1S,7S)-1-(5-amino-2-fluorophenyl)-4-thia-2-azabicyclo[5.1.0]oct-2-en-3-ylcarbamate

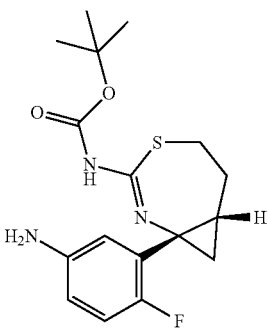 [SMILES: CC(C)(C)OC(=O)NC1=N[C@@]2(c3cc(N)ccc3F)C[C@H]2CCS1]

Prepared in an analogous manner as described for intermediate rac-A8a from tert-butyl (1S,7S)-1-(5-amino-2-fluorophenyl)-4-thia-2-azabicyclo[5.1.0]oct-2-en-3-ylcarbamate (intermediate (−)-A7a) (210 mg, 0.55 mmol) to give the tert-butyl (1S,7S)-1-(5-amino-2-fluorophenyl)-4-thia-2-azabicyclo[5.1.0]oct-2-en-3-ylcarbamate (174 mg, 90%) as a grey foam. MS (ISP): m/z=352.3 [(M+H)$^+$].

Intermediate rac-A8b: tert-butyl (1SR,7SR)-1-(5-amino-2-chlorophenyl)-4-thia-2-azabicyclo[5.1.0]oct-2-en-3-ylcarbamate

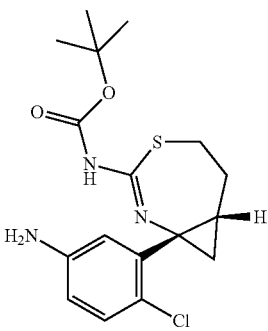 [SMILES: CC(C)(C)OC(=O)NC1=N[C@@]2(c3cc(N)ccc3Cl)C[C@H]2CCS1]

Prepared in an analogous manner as described for intermediate rac-A8a from tert-butyl (1SR,7SR)-1-(2-chloro-5-nitrophenyl)-4-thia-2-azabicyclo[5.1.0]oct-2-en-3-ylcarbamate (intermediate rac-A7b) (72 mg, 181 μmol) to give the tert-butyl (1SR,7SR)-1-(5-amino-2-chlorophenyl)-4-thia-2-azabicyclo[5.1.0]oct-2-en-3-ylcarbamate (56 mg, 152 μmol, 84.1% yield) as a grey foam. MS (ISP): m/z=268.1 [(M−Boc+H)$^+$] and 270.2 [(M−Boc+2+H)$^+$].

Intermediate rac-A8c: tert-Butyl (1SR,7SR)-1-(3-aminophenyl)-4-thia-2-azabicyclo[5.1.0]oct-2-en-3-ylcarbamate

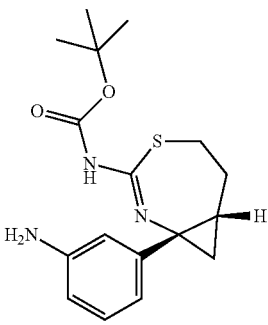 [SMILES: CC(C)(C)OC(=O)NC1=N[C@@]2(c3cccc(N)c3)C[C@H]2CCS1]

Prepared in an analogous manner as described for intermediate rac-A8a from tert-butyl (1SR,7SR)-1-(3-nitrophenyl)-4-thia-2-azabicyclo[5.1.0]oct-2-en-3-ylcarbamate (intermediate rac-A7c) (255 mg, 702 μmol) to give the tert-butyl (1SR,7SR)-1-(3-aminophenyl)-4-thia-2-azabicyclo[5.1.0]oct-2-en-3-ylcarbamate (204 mg, 612 μmol, 87.2% yield) as a grey foam. MS (ISP): m/z=334.2 [(M+H)$^+$].

Intermediate (−)-A8c: tert-butyl (1S,7S)-1-(3-aminophenyl)-4-thia-2-azabicyclo[5.1.0]oct-2-en-3-ylcarbamate

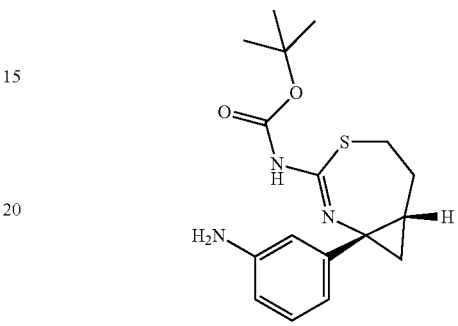

Prepared in an analogous manner as described for intermediate rac-A8a from tert-butyl (1S,7S)-1-(3-nitrophenyl)-4-thia-2-azabicyclo[5.1.0]oct-2-en-3-ylcarbamate (intermediate (−)-A7c) (320 mg, 0.88 mmol) to give the tert-butyl (1S,7S)-1-(3-aminophenyl)-4-thia-2-azabicyclo[5.1.0]oct-2-en-3-ylcarbamate (280 mg, 0.84 mmol, 95.4% yield) as a grey foam. MS (ISP): m/z=334.3 [(M+H)$^+$].

Intermediate rac-A9a: tert-Butyl (1SR,7SR)-1-(5-(5-chloropicolinamido)-2-fluorophenyl)-4-thia-2-azabicyclo[5.1.0]oct-2-en-3-ylcarbamate

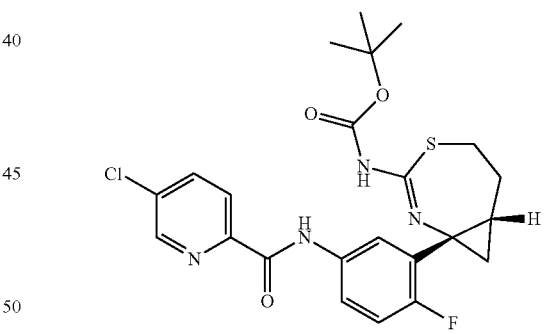

Commercially available 5-chloro-2-pyridinecarboxylic acid (30 mg, 0.19 mmol) was dissolved in dichloromethane (3 ml) and DMF (1 ml), then diisopropylethylamine (85 μl, 0.50 mmol) and 1-[bis(dimethylamino)methylene]-1H-1,2,3-triazolo[4,5-b]pyridinium-3-oxide hexafluorophosphate (HATU) (87 mg, 0.23 mmol) were added at 23° C. After 15 min of stiffing tert-butyl (1SR,7SR)-1-(5-amino-2-fluorophenyl)-4-thia-2-azabicyclo[5.1.0]oct-2-en-3-ylcarbamate (intermediate rac-A8a) (53 mg, 0.15 mmol) was added. The brown solution was stirred for 20 hours at 23° C. The grey reaction mixture was poured on ice cold sat. NaHCO$_3$ solution and extracted twice with dichloromethane. The organic layers were washed with brine, dried over Na$_2$SO$_4$, filtered and evaporated to give a brown oil which was chromatographed on 5 g silica gel with cyclohexane/ethyl acetate 1:1 to give the tert-butyl (1SR,7SR)-1-(5-(5-chloropicolinamido)-2-fluorophenyl)-4-thia-2-azabicyclo[5.1.0]oct-2-en-3-ylcarbamate (29 mg; 31%) as a light yellow oil. MS (ISP): m/z=491.1 [(M+H)⁺] and 493.2 [(M+2+H)⁺].

Intermediate (−)-A9a: tert-Butyl (1S,7S)-1-(5-(5-chloropicolinamido)-2-fluorophenyl)-4-thia-2-azabicyclo[5.1.0]oct-2-en-3-ylcarbamate

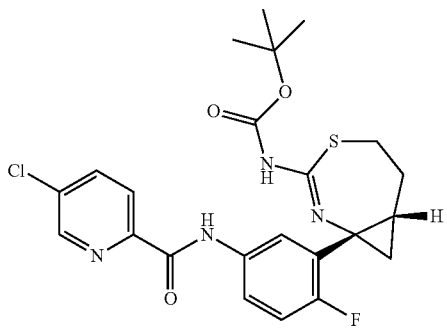 [SMILES: CC(C)(C)OC(=O)NC1=N[C@@]2(c3cc(NC(=O)c4ccc(Cl)cn4)ccc3F)C[C@H]2CCS1]

Prepared in an analogous manner as described for intermediate rac-A9a from tert-butyl (1S,7S)-1-(5-amino-2-fluorophenyl)-4-thia-2-azabicyclo[5.1.0]oct-2-en-3-ylcarbamate (intermediate (−)-A8a) (85 mg, 0.24 mmol) and 5-chloro-2-pyridinecarboxylic acid to give the tert-butyl (1S,7S)-1-(5-(5-chloropicolinamido)-2-fluorophenyl)-4-thia-2-azabicyclo[5.1.0]oct-2-en-3-ylcarbamate (70 mg, 50% yield) as a light yellow oil. MS (ISP): m/z=391.0 [(M-Boc+H)⁺] and 393.1 [(M-Boc+2+H)⁺].

Intermediate (−)-A9b: tert-Butyl (1S,7S)-1-(5-(5-cyanopicolinamido)-2-fluorophenyl)-4-thia-2-azabicyclo[5.1.0]oct-2-en-3-ylcarbamate

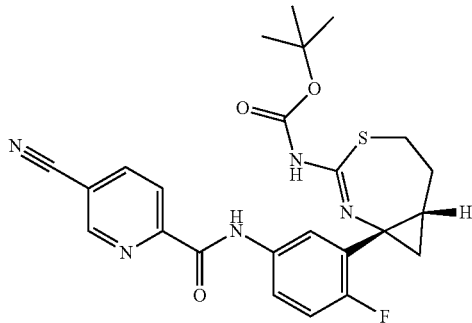 [SMILES: CC(C)(C)OC(=O)NC1=N[C@@]2(c3cc(NC(=O)c4ccc(C#N)cn4)ccc3F)C[C@H]2CCS1]

Prepared in an analogous manner as described for intermediate rac-A9a from tert-butyl (1S,7S)-1-(5-amino-2-fluorophenyl)-4-thia-2-azabicyclo[5.1.0]oct-2-en-3-ylcarbamate (intermediate (−)-A8a) (86.7 mg, 247 μmol) and commercially available 5-cyanopicolinic acid to give the tert-butyl (1S,7S)-1-(5-(5-cyanopicolinamido)-2-fluorophenyl)-4-thia-2-azabicyclo[5.1.0]oct-2-en-3-ylcarbamate (65 mg, 135 μmol, 46.5% yield) as a yellow oil. MS (ISP): m/z=482.1 [(M+H)⁺].

Intermediate rac-A9c: tert-Butyl (1SR,7SR)-1-(2-chloro-5-(5-chloropicolinamido)phenyl)-4-thia-2-azabicyclo[5.1.0]oct-2-en-3-ylcarbamate

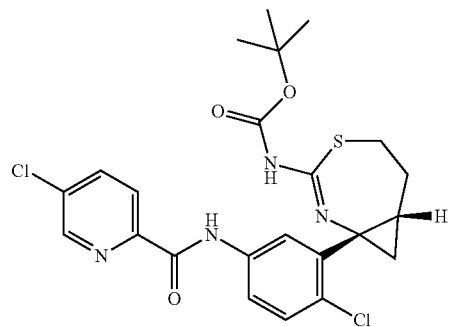 [SMILES: CC(C)(C)OC(=O)NC1=N[C@@]2(c3cc(NC(=O)c4ccc(Cl)cn4)ccc3Cl)C[C@H]2CCS1]

Prepared in an analogous manner as described for intermediate rac-A9a from tert-butyl (1SR,7SR)-1-(5-amino-2-chlorophenyl)-4-thia-2-azabicyclo[5.1.0]oct-2-en-3-ylcarbamate (intermediate rac-A8b) (56 mg, 152 μmol) and 5-chloro-2-pyridinecarboxylic acid to give the tert-butyl (1SR,7SR)-1-(2-chloro-5-(5-chloropicolinamido)phenyl)-4-thia-2-azabicyclo[5.1.0]oct-2-en-3-ylcarbamate (42 mg, 82.8 μmol, 54.4% yield) as a light brown oil. MS (ISP): m/z=407.2 [(M-Boc+H)⁺], 409.2 [(M-Boc+2+H)⁺] and 411.0 [(M-Boc+4+H)⁺].

Intermediate rac-A9d: tert-Butyl (1SR,7SR)-1-(3-(5-chloropicolinamido)phenyl)-4-thia-2-azabicyclo[5.1.0]oct-2-en-3-ylcarbamate

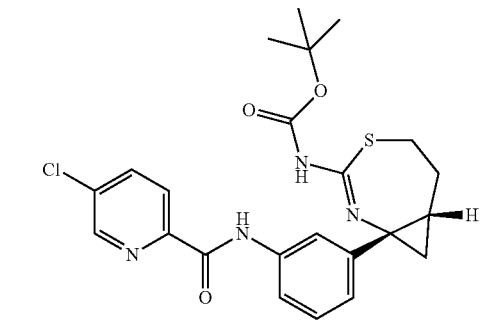 [SMILES: CC(C)(C)OC(=O)NC1=N[C@@]2(c3cccc(NC(=O)c4ccc(Cl)cn4)c3)C[C@H]2CCS1]

Prepared in an analogous manner as described for intermediate rac-A9a from tert-butyl tert-butyl (1SR,7SR)-1-(3-aminophenyl)-4-thia-2-azabicyclo[5.1.0]oct-2-en-3-ylcarbamate (intermediate rac-A8c) (100 mg, 300 μmol) and 5-chloro-2-pyridinecarboxylic acid to give the tert-butyl (1SR,7SR)-1-(3-(5-chloropicolinamido)phenyl)-4-thia-2-azabicyclo[5.1.0]oct-2-en-3-ylcarbamate (134 mg, 283 μmol, 94.5% yield) as a brown oil. MS (ISP): m/z=373.0 [(M-Boc+H)⁺] and 375.0 [(M-Boc+2+H)⁺].

Intermediate (−)-A9d: tert-Butyl (1S,7S)-1-(3-(5-chloropicolinamido)phenyl)-4-thia-2-azabicyclo[5.1.0]oct-2-en-3-ylcarbamate

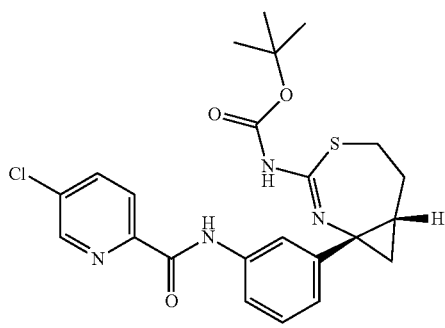 [SMILES: CC(C)(C)OC(=O)NC1=N[C@@]2(c3cccc(NC(=O)c4ccc(Cl)cn4)c3)C[C@H]2CCS1]

Prepared in an analogous manner as described for intermediate rac-A9a from tert-butyl tert-butyl (1S,7S)-1-(3-aminophenyl)-4-thia-2-azabicyclo[5.1.0]oct-2-en-3-ylcarbamate (intermediate (−)-A8c) (125 mg, 375 μmol) and 5-chloro-2-pyridinecarboxylic acid to give the tert-butyl (1S,7S)-1-(3-(5-chloropicolinamido)phenyl)-4-thia-2-azabicyclo[5.1.0]oct-2-en-3-ylcarbamate (118 mg, 249 μmol, 66.6% yield) as a light brown gum. MS (ISP): m/z=473.1 [(M+H)$^+$] and 475.1 [(M+2+H)$^+$].

Intermediate rac-A9e: tert-Butyl (1SR,7SR)-1-(3-(5-cyanopicolinamido)phenyl)-4-thia-2-azabicyclo[5.1.0]oct-2-en-3-ylcarbamate

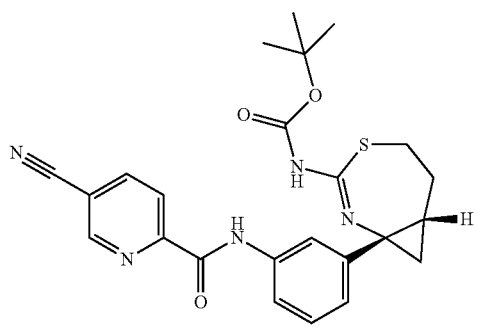 [SMILES: CC(C)(C)OC(=O)NC1=N[C@@]2(c3cccc(NC(=O)c4ccc(C#N)cn4)c3)C[C@H]2CCS1]

Prepared in an analogous manner as described for intermediate rac-A9a from tert-butyl tert-butyl (1SR,7SR)-1-(3-aminophenyl)-4-thia-2-azabicyclo[5.1.0]oct-2-en-3-ylcarbamate (intermediate rac-A8c) (100 mg, 300 μmol) and 5-cyanopicolinic acid to give the tert-butyl (1SR,7SR)-1-(3-(5-cyanopicolinamido)phenyl)-4-thia-2-azabicyclo[5.1.0]oct-2-en-3-ylcarbamate (105 mg, 227 μmol, 75.5% yield) as a yellow gum. MS (ISP): m/z=364.1 [(M-Boc+H)$^+$].

Intermediate (−)-A9e: tert-Butyl (1S,7S)-1-(3-(5-cyanopicolinamido)phenyl)-4-thia-2-azabicyclo[5.1.0]oct-2-en-3-ylcarbamate

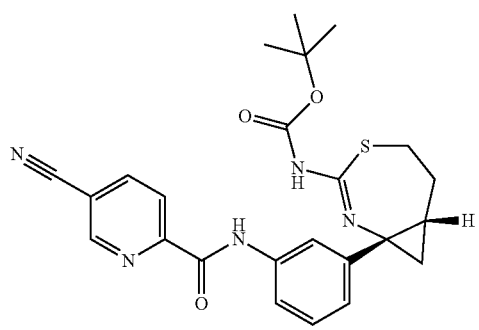 [SMILES: CC(C)(C)OC(=O)NC1=N[C@@]2(c3cccc(NC(=O)c4ccc(C#N)cn4)c3)C[C@H]2CCS1]

Prepared in an analogous manner as described for intermediate rac-A9a from tert-butyl tert-butyl (1S,7S)-1-(3-aminophenyl)-4-thia-2-azabicyclo[5.1.0]oct-2-en-3-ylcarbamate (intermediate (−)-A8c) (125 mg, 375 μmol) and 5-cyanopicolinic acid to give the tert-butyl (1S,7S)-1-(3-(5-cyanopicolinamido)phenyl)-4-thia-2-azabicyclo[5.1.0]oct-2-en-3-ylcarbamate (136 mg, 293 μmol, 78.3% yield) as a brown gum. MS (ISP): m/z=464.2 [(M+H)$^+$].

Intermediate B2a: 2-(3-Nitrophenyl)acetyl chloride

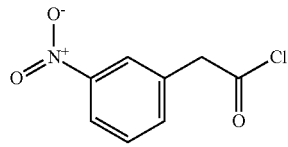 [SMILES: O=C(Cl)Cc1cccc([N+](=O)[O-])c1]

A mixture of commercially available 2-(3-nitrophenyl)acetic acid [CAS no. 1877-73-2] (25.8 g, 142 mmol, Eq: 1.00) and thionyl chloride (25.4 g, 15.5 ml, 214 mmol, Eq: 1.5) in toluene (141 ml) and DMF (208 mg, 221 μl, 2.85 mmol, Eq: 0.02) was stirred at 80° C. for 2 h. The hot solution was filtered through a Sartorius filter, the filtrate was evaporated and dried in HV to give the 2-(3-nitrophenyl)acetyl chloride (28.12 g, 141 mmol, 98.9% yield) as a yellow solid, which was used without further purification.

Intermediate B3a: Allyl 2-(3-nitrophenyl)acetate

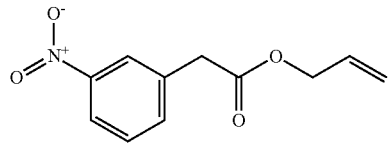 [SMILES: C=CCOC(=O)Cc1cccc([N+](=O)[O-])c1]

To a solution of allyl alcohol (48.3 g, 56.5 ml, 831 mmol, Eq: 10) and triethylamine (12.6 g, 17.4 ml, 125 mmol, Eq: 1.5) at 0° C. was added 2-(3-nitrophenyl)acetyl chloride (intermediate B2a) (16.59 g, 83.1 mmol, Eq: 1.00) and the mixture was stirred at 0 to 23° C. for 2 h. Poured into water, extracted with ethyl acetate, washed organic layer with brine and dried over Na$_2$SO$_4$. Removal of the solvent in vacuum left a light brown oil, which was purified by silica gel flash chromatography with n-heptane/ethyl acetate to give the title compounds as a yellow liquid (14.89 g, 81%).

Intermediate B4a: Allyl 2-diazo-2-(3-nitrophenyl)acetate

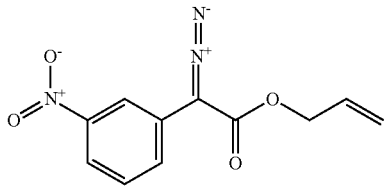 [SMILES: C=CCOC(=O)C(=[N+]=[N-])c1cccc([N+](=O)[O-])c1]

To a solution of 1,8-diazabicyclo[5.4.0]undec-7-ene (10.6 g, 10.5 ml, 69.6 mmol, Eq: 1.04) in THF (59.0 ml) at 5° C. was added dropwise a solution of allyl 2-(3-nitrophenyl)acetate (intermediate B3a) (14.8 g, 66.9 mmol, Eq: 1.00) and 4-acetamidobenzenesulfonyl azide (16.6 g, 68.9 mmol, Eq: 1.03) in THF (118 ml) within 40 min and the mixture was stirred at 23° C. for 18 h protected from light. Quenched with sat. NH4Cl-sol., diluted with ethyl acetate, separated phases, the organic layer was washed with brine and dried over Na2SO4. Removal of the solvent in vacuum left an orange semisolid, diluted with diethyl ether, filtered the solid off, washed with diethyl ether, the filtrate was concentrated in vacuum to give an orange semisolid. The crude material was purified by flash chromatography (silica gel, 300 g, 25% to 30% EtOAc in heptane) to give the title compound as a yellow solid (15.62 g, 94%).

Intermediate B5a: (1SR,5RS)-1-(3-Nitrophenyl)-3-oxabicyclo[3.1.0]hexan-2-one

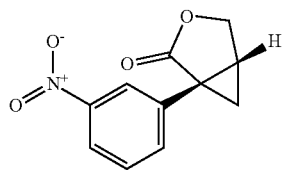 [SMILES: O=C1OC[C@@H]2C[C@]12c1cccc([N+](=O)[O-])c1]

To a solution of commercially available rhodium(II) octanoate dimer (Rh2(C7H16CO2)4) CAS-no. [73482-96-9] (440 mg, 565 µmol, Eq: 0.00941) in dichloromethane (180 ml) at 50° C. was added a solution of allyl 2-diazo-2-(3-nitrophenyl)acetate (intermediate B4a) (14.85 g, 60.1 mmol, Eq: 1.00) in dichloromethane (38 ml) via syringe pump within 18 h. Refluxing was continued for 30 min, the solvent was evaporated and the crude material was purified by flash chromatography (silica gel, 70 g, 0% to 100% EtOAc in heptane) to give (1SR,5RS)-1-(3-nitrophenyl)-3-oxabicyclo [3.1.0]hexan-2-one (12 g, 54.7 mmol, 91.1% yield) as a light brown solid. [cf. Adv. Synth. Catal. 2001, 343, 299 for an enantioselective version of this reaction]. MS (ISP): m/z=237.1 [(M+NH4)+].

Intermediate B6a: (1SR,2RS)-2-(Hydroxymethyl)-1-(3-nitrophenyl)cyclopropanecarboxamide

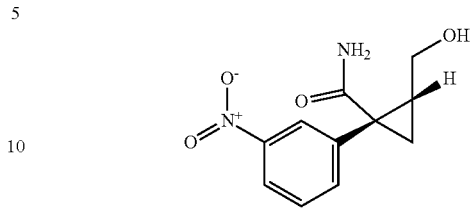

A mixture of (1SR,5RS)-1-(3-nitrophenyl)-3-oxabicyclo [3.1.0]hexan-2-one (intermediate B5a) (11.47 g, 52.3 mmol, Eq: 1.00) in ammonia (7 M in MeOH) (140 ml, 980 mmol, Eq: 18.7) was stirred in 10 sealed tubes at 60° C. for 3.5 days, but still not complete (ca. 75% conversion). Evaporated all volatiles, coated on silica gel and the crude material was purified by flash chromatography (silica gel, 200 g, 70% to 100% EtOAc in heptane to EtOH/THF 3:1->2:1) to give recovered (1SR,5RS)-1-(3-nitrophenyl)-3-oxabicyclo[3.1.0]hexan-2-one (1.957 g, 16%, which was converted under the same conditions to product) and (1SR,2RS)-2-(hydroxymethyl)-1-(3-nitrophenyl)cyclopropanecarboxamide (10.61 g, 44.9 mmol, 85.8% yield) as a light brown solid. MS (ISN): m/z=235.1 [(M−H)−].

Intermediate B7a: Methyl (1SR,2RS)-2-(hydroxymethyl)-1-(3-nitrophenyl)cyclopropylcarbamate

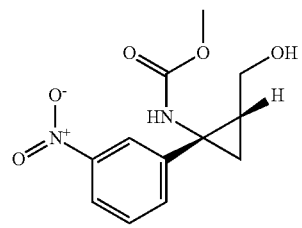 [SMILES: COC(=O)N[C@@]1(c2cccc([N+](=O)[O-])c2)C[C@H]1CO]

Preparation of the oxidizing reagent: KOH (85%, 24.75 g, 375 mmol) was dissolved in H2O (150 mL), cooled to −5° C., N-bromosuccinimide (26.7 g, 150 mmol) was added and stirred at −5° C. until all the solid had dissolved. The resulting clear yellow solution was aged at −3 to −5° C. for 24 h, then was stored in the freezer and thawed in the fridge, resulting in a light yellow clear solution of the oxidizing reagent (ca. 1 M). To a suspension of (1SR,2RS)-2-(hydroxymethyl)-1-(3-nitrophenyl)cyclopropanecarboxamide (intermediate B6a) (10.61 g, 44.9 mmol, Eq: 1.00) in tetrahydrofuran (265 ml) and methanol (186 ml) at 0° C. was added a solution of the above prepared reagent (ca. 1 M, 17 ml) and the mixture was stirred at 0 to 23° C. for 18 h. Concentrated in vacuum, acidified with conc. HCl to pH=1, extracted twice with EtOAc, washed the combined organic layer with sat. NaHCO3-sol. and brine, dried over Na2SO4. Removal of the solvent in vacuum left a brown oil (12.82 g). The crude material was purified by flash chromatography (silica gel, 300 g, 35% to 100% EtOAc in heptane) to give the title methyl (1SR,2RS)-2-(hydroxymethyl)-1-(3-nitrophenyl)cyclopropylcarbamate (4.5 g, 16.9 mmol, 37.6% yield) as a light yellow solid. MS (ISP): m/z=267.2 [(M+H)+]. Also isolated (1SR,6RS)-1-(3-nitrophenyl)-4-oxa-2-azabicyclo[4.1.0] heptan-3-one (3.55 g, 15.2 mmol, 33.8% yield) as a light yellow solid, which was converted into the title carbamate (3.52 g, 94.5% yield) by the following sequence:

Step a) A mixture of (1SR,6RS)-1-(3-nitrophenyl)-4-oxa-2-azabicyclo[4.1.0]heptan-3-one (3.55 g, 15.2 mmol, Eq: 1.00) and lithium hydroxide monohydrate (6.36 g, 152 mmol, Eq: 10) in water (40 ml) and ethanol (8 ml) was stirred at 100° C. for 1.75 h. Cooled to 23° C., huge precipitate (salt of the carbamic acid), acidified with conc. HCl to pH<1 ($CO_2$ evolution!), stirred at 23° C. for 5 min, made alkaline with 10 M NaOH-sol., extracted thrice with dichloromethane, dried combined organic layer over $Na_2SO_4$. Removal of the solvent in vacuum left the ((1RS,2SR)-2-amino-2-(3-nitrophenyl)cyclopropyl)methanol (3.085 g, 14.8 mmol, 97.8% yield) as a brown oil.

Step b) To a solution of ((1RS,2SR)-2-amino-2-(3-nitrophenyl)cyclopropyl)methanol (2.85 g, 13.7 mmol, Eq: 1.00) in dichloromethane (27.4 ml) was added at 5° C. diisopropylethylamine (2.65 g, 3.59 ml, 20.5 mmol, Eq: 1.5) and methyl chloroformate (1.42 g, 1.17 ml, 15.1 mmol, Eq: 1.1) dropwise via syringe. The reaction mixture was stirred at rt for 16 hours. The reaction mixture was extracted with sat $NaHCO_3$ solution and dichloromethane. The organic layer was washed with water and brine, the aqueous layers were reextracted with dichloromethane. The combined organic layers were dried over $Na_2SO_4$, filtered and evaporated to give a brown oil which was purified by silica gel flash chromatography with 0-100% EtOAc in heptane to give the title methyl (1SR,2RS)-2-(hydroxymethyl)-1-(3-nitrophenyl)cyclopropylcarbamate (3.52 g, 13.2 mmol, 96.6% yield) as a light brown oil.

Intermediate B8a: ((1RS,2SR)-2-(Methoxycarbonylamino)-2-(3-nitrophenyl)cyclopropyl)methyl methanesulfonate

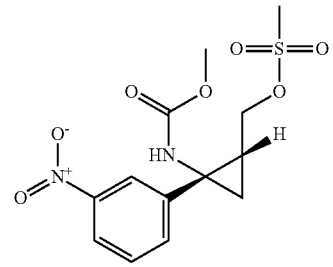 [SMILES: COC(=O)N[C@@]1(c2cccc([N+](=O)[O-])c2)C[C@H]1COS(C)(=O)=O]

To a solution of methyl (1SR,2RS)-2-(hydroxymethyl)-1-(3-nitrophenyl)cyclopropylcarbamate (intermediate B7a) (3.5 g, 13.1 mmol, Eq: 1.00) in dichloromethane (20 ml) at 0° C. was added triethylamine (2.66 g, 3.66 ml, 26.3 mmol, Eq: 2.00) followed by dropwise addition of methanesulfonyl chloride (2.26 g, 1.54 ml, 19.7 mmol, Eq: 1.50) and the mixture was stirred at 0° C. for 2 h. Poured into ice cold 1 M HCl-sol., extracted with tert-butyl methyl ether, washed organic layer with sat. $NaHCO_3$-sol. and brine, dried over $Na_2SO_4$. Removal of the solvent in vacuum left a yellow oil. MS (ISP): m/z=362.1 [(M+$NH_4$)$^+$].

Intermediate B9a: Methyl (1SR,2SR)-2-(cyanomethyl)-1-(3-nitrophenyl)cyclopropylcarbamate

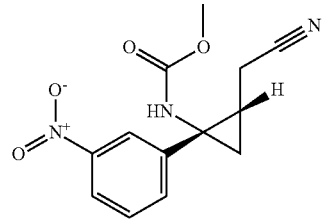 [SMILES: COC(=O)N[C@@]1(c2cccc([N+](=O)[O-])c2)C[C@H]1CC#N]

A mixture of ((1RS,2SR)-2-(methoxycarbonylamino)-2-(3-nitrophenyl)cyclopropyl)methyl methanesulfonate (intermediate B8a) (4.53 g, 13.2 mmol, Eq: 1.00), potassium cyanide (1.11 g, 17.1 mmol, Eq: 1.3) and tetrabutylammonium iodide (486 mg, 1.32 mmol, Eq: 0.1) in DMSO (13 ml) was stirred at 23° C. for 18 h. Poured into ice water, extracted with EtOAc, washed organic layer with brine, reextracted combined aqueous layer with EtOAc, dried combined organic layer over Na2SO4. Removal of the solvent in vacuum left a dark brown oil (8370-1/1; HPLC 1.775 min 60%, 2.070 min 27%, 2.262 min 13%). The crude material was purified by flash chromatography (silica gel, 50 g, 0% to 60% EtOAc in heptane) to give the methyl (1SR,2SR)-2-(cyanomethyl)-1-(3-nitrophenyl)cyclopropylcarbamate (2.318 g, 8.42 mmol, 64.0% yield) as a yellow gum. MS (ISP): m/z=276.1 [(M+H)$^+$].

Intermediate B10a: Ethyl 2-((1SR,2SR)-2-(methoxycarbonylamino)-2-(3-nitrophenyl)cyclopropyl)acetate

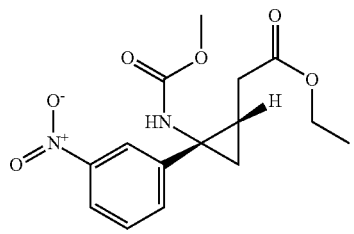 [SMILES: CCOC(=O)C[C@@H]1C[C@@]1(NC(=O)OC)c1cccc([N+](=O)[O-])c1]

To a solution of methyl (1SR,2SR)-2-(cyanomethyl)-1-(3-nitrophenyl)cyclopropylcarbamate (intermediate B9a) (2.1 g, 7.63 mmol, Eq: 1.00) in ethanol (40 ml) was added dropwise thionyl chloride (13.6 g, 8.35 ml, 114 mmol, Eq: 15) ant the light brown solution was stirred at 80° C. for 1 hour. Poured cautiously into sat $NaHCO_3$ solution, extracted with dichloromethane, washed the organic layer with brine and dried over $Na_2SO_4$. Removal of the solvent in vacuum left the ethyl 2-((1SR,2SR)-2-(methoxycarbonylamino)-2-(3-nitrophenyl)cyclopropyl)acetate (2.54 g, 7.49 mmol, 98.1% yield) as a light brown oil. MS (ISP): m/z=323.2 [(M+H)$^+$].

Intermediate B11a: Methyl (1SR,2SR)-2-(2-hydroxyethyl)-1-(3-nitrophenyl)cyclopropylcarbamate

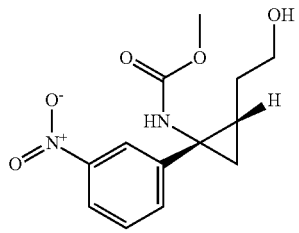 [SMILES: COC(=O)N[C@@]1(c2cccc([N+](=O)[O-])c2)C[C@H]1CCO]

Ethyl 2-((1SR,2SR)-2-(methoxycarbonylamino)-2-(3-nitrophenyl)cyclopropyl)acetate (intermediate B10a) (2.45 g, 7.6 mmol, Eq: 1.00) was dissolved in tetrahydrofuran (80 ml) and lithium borohydride (2 M in THF; 8.36 ml, 16.7 mmol, Eq: 2.2) was added dropwise at 5° C. The turbid solution was stirred at 23° C. for 6 hours. The reaction mixture was poured into ice water, sat NH$_4$Cl solution (100 ml) was added slowly and the mixture was stirred vigorously for 45 min (gas evolution finished). Then extraction with EtOAc, the organic layer was dried over Na$_2$SO$_4$, filtration and evaporation of the solvent left a yellow oil (2.5 g; 117%). Crystallization with dichloromethane/cyclohexane gives the methyl (1SR,2SR)-2-(2-hydroxyethyl)-1-(3-nitrophenyl)cyclopropylcarbamate (1.84 g, 6.56 mmol, 86.4% yield) as a light yellow solid. MS (ISP): m/z=281.1 [(M+H)$^+$].

Example 1

5-Chloro-pyridine-2-carboxylic acid [3-((1SR,7SR)-3-amino-4-thia-2-aza-bicyclo[5.1.0]oct-2-en-1-yl)-4-fluoro-phenyl]-amide

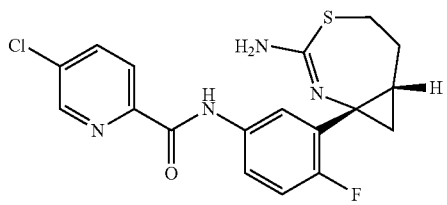

tert-Butyl (1SR,7SR)-1-(5-(5-chloropicolinamido)-2-fluorophenyl)-4-thia-2-azabicyclo[5.1.0]oct-2-en-3-ylcarbamate (intermediate rac-A9a) (29 mg; 0.06 mmol) was dissolved in dichloromethane (3 ml) and at 23° C. trifluoroacetic acid (TFA) (0.8 ml) was added. The yellow solution was stirred for 2 hours at 23° C. The reaction mixture was extracted with sat NaHCO$_3$ solution and dichloromethane. The organic layer was washed with water and brine, the aqueous layers were reextracted with dichloromethane. The combined organic layers were dried over Na$_2$SO$_4$, filtered and evaporated to give a light yellow oil which was chromatographed on 10 g SiO$_2$—NH$_2$ with dichloromethane+dichloromethane/methanol 19:1 to give the 5-chloro-pyridine-2-carboxylic acid [3-((1SR,7SR)-3-amino-4-thia-2-aza-bicyclo[5.1.0]oct-2-en-1-yl)-4-fluoro-phenyl]-amide (13.34 mg; 58%) as an off white solid. MS (ISP): m/z=391.0 [(M+H)$^+$] and 393.1 [(M+2+H)$^+$].

Example 2

5-Chloro-pyridine-2-carboxylic acid [3-((1S,7S)-3-amino-4-thia-2-aza-bicyclo[5.1.0]oct-2-en-1-yl)-4-fluoro-phenyl]-amide

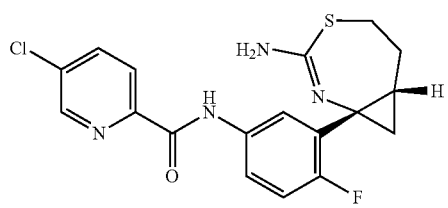

Prepared in an analogous manner as described for example 1 from tert-butyl (1S,7S)-1-(5-(5-chloropicolinamido)-2-fluorophenyl)-4-thia-2-azabicyclo[5.1.0]oct-2-en-3-ylcarbamate (intermediate (−)-A9a) (60 mg, 0.12 mmol) to give the 5-chloro-pyridine-2-carboxylic acid [3-((1S,7S)-3-amino-4-thia-2-aza-bicyclo[5.1.0]oct-2-en-1-yl)-4-fluoro-phenyl]-amide (33 mg, 59% yield) as an off-white solid. MS (ISP): m/z=391.0 [(M+H)$^+$] and 393.1 [(M+2+H)$^+$]. Optical rotation: −176.0°; 589 nm, c=0.241; CHCl$_3$; 20° C.

Example 3

5-Cyano-pyridine-2-carboxylic acid [3-((1S,7S)-3-amino-4-thia-2-aza-bicyclo[5.1.0]oct-2-en-1-yl)-4-fluoro-phenyl]-amide

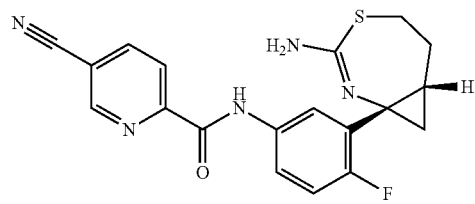 [SMILES: N#Cc1ccc(C(=O)Nc2ccc(F)c([C@]34C[C@H]3CCSC(N)=N4)c2)nc1]

Prepared in an analogous manner as described for example 1 from tert-butyl (1S,7S)-1-(5-(5-cyanopicolinamido)-2-fluorophenyl)-4-thia-2-azabicyclo[5.1.0]oct-2-en-3-ylcarbamate (intermediate (−)-A9b) (65 mg, 135 μmol) to give the N-(3-((1S,7S)-3-amino-4-thia-2-azabicyclo[5.1.0]oct-2-en-1-yl)-4-fluorophenyl)-5-cyanopicolinamide (24 mg, 62.9 μmol, 46.6% yield) as a light brown solid. MS (ISP): m/z=382.2 [(M+H)$^+$].

Example 4

N-(3-((1SR,7SR)-3-amino-4-thia-2-azabicyclo[5.1.0]oct-2-en-1-yl)-4-chlorophenyl)-5-chloropicolinamide

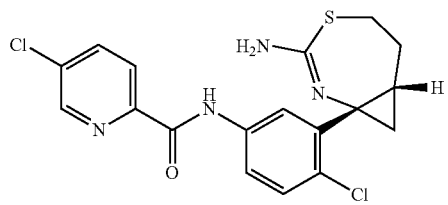 [SMILES: NC1=N[C@@]2(c3cc(NC(=O)c4ccc(Cl)cn4)ccc3Cl)C[C@H]2CCS1]

Prepared in an analogous manner as described for example 1 from tert-butyl (1SR,7SR)-1-(2-chloro-5-(5-chloropicolinamido)phenyl)-4-thia-2-azabicyclo[5.1.0]oct-2-en-3-ylcarbamate (intermediate rac-A9c) (42 mg, 82.8 μmol) to give the N-(3-((1SR,7SR)-3-amino-4-thia-2-azabicyclo[5.1.0]oct-2-en-1-yl)-4-chlorophenyl)-5-chloropicolinamide (9.29 mg, 22.8 μmol, 27.6% yield) as an off-white solid. MS (ISP): m/z=407.2 [(M+H)$^+$] and 409.1 [(M+2+H)$^+$].

Example 5

N-(3-((1SR,7SR)-3-Amino-4-thia-2-azabicyclo[5.1.0]oct-2-en-1-yl)phenyl)-5-chloropicolinamide

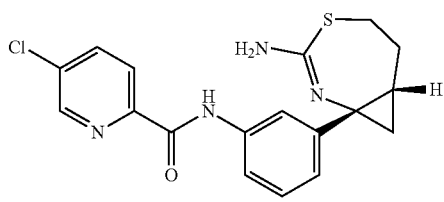 [SMILES: NC1=N[C@@]2(c3cccc(NC(=O)c4ccc(Cl)cn4)c3)C[C@H]2CCS1]

Prepared in an analogous manner as described for example 1 from tert-butyl (1SR,7SR)-1-(3-(5-chloropicolinamido)phenyl)-4-thia-2-azabicyclo[5.1.0]oct-2-en-3-ylcarbamate (intermediate rac-A9d) (132 mg, 279 μmol) to give the N-(3-((1SR,7SR)-3-amino-4-thia-2-azabicyclo[5.1.0]oct-2-en-1-yl)phenyl)-5-chloropicolinamide (49 mg, 131 μmol, 47.1% yield) as an off-white foam. MS (ISP): m/z=373.0 [(M+H)$^+$] and 375.0 [(M+2+H)$^+$].

Example 6

N-(3-((1SR,7SR)-3-Amino-4-thia-2-azabicyclo[5.1.0]oct-2-en-1-yl)phenyl)-5-cyanopicolinamide

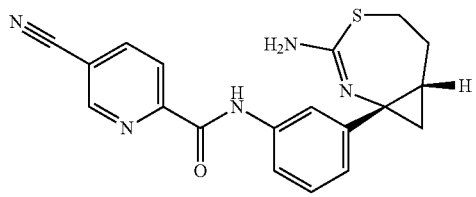 [SMILES: N#Cc1ccc(C(=O)Nc2cccc([C@]34C[C@H]3CCSC(N)=N4)c2)nc1]

Prepared in an analogous manner as described for example 1 from tert-butyl (1SR,7SR)-1-(3-(5-cyanopicolinamido)phenyl)-4-thia-2-azabicyclo[5.1.0]oct-2-en-3-ylcarbamate (intermediate rac-A9e) (99 mg, 214 μmol) to give the N-(3-((1SR,7SR)-3-amino-4-thia-2-azabicyclo[5.1.0]oct-2-en-1-yl)phenyl)-5-cyanopicolinamide (51 mg, 140 μmol, 65.7% yield) as a white solid. MS (ISP): m/z=364.1 [(M+H)$^+$].

Example 7

N-(3-((1S,7S)-3-Amino-4-thia-2-azabicyclo[5.1.0]oct-2-en-1-yl)phenyl)-5-chloropicolinamide

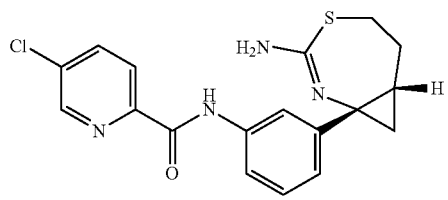 [SMILES: NC1=N[C@@]2(c3cccc(NC(=O)c4ccc(Cl)cn4)c3)C[C@H]2CCS1]

Prepared in an analogous manner as described for example 1 from tert-butyl (1S,7S)-1-(3-(5-chloropicolinamido)phenyl)-4-thia-2-azabicyclo[5.1.0]oct-2-en-3-ylcarbamate (intermediate (−)-A9d) (115 mg, 243 μmol) to give the N-(3-((1S,7S)-3-amino-4-thia-2-azabicyclo[5.1.0]oct-2-en-1-yl)phenyl)-5-chloropicolinamide (48 mg, 129 μmol, 52.9% yield) as a white foam. MS (ISP): m/z=373.0 [(M+H)$^+$] and 375.1 [(M+2+H)$^+$].

Example 8

N-(3-((1S,7S)-3-Amino-4-thia-2-azabicyclo[5.1.0]oct-2-en-1-yl)phenyl)-5-cyanopicolinamide

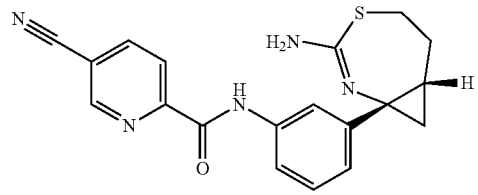 [SMILES: N#Cc1ccc(C(=O)Nc2cccc([C@]34C[C@H]3CCSC(N)=N4)c2)nc1]

Prepared in an analogous manner as described for example 1 from tert-butyl (1S,7S)-1-(3-(5-cyanopicolinamido)phenyl)-4-thia-2-azabicyclo[5.1.0]oct-2-en-3-ylcarbamate (intermediate (−)-A9e) (136 mg, 293 μmol) to give the N-(3-((1S,7S)-3-amino-4-thia-2-azabicyclo[5.1.0]oct-2-en-1-yl)phenyl)-5-cyanopicolinamide (56 mg, 154 μmol, 52.5% yield) as an off-white solid. MS (ISP): m/z=364.1 [(M+H)$^+$].

The invention claimed is:
1. A compound of formula I,

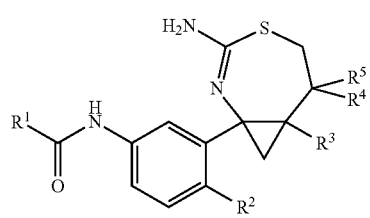

I wherein
$R^1$ is selected from the group consisting of
i) heteroaryl and
ii) heteroaryl substituted by 1-2 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkenyl, $C_{2-6}$-alkynyl and $C_{1-6}$-alkyl;

$R^2$ is selected from the group consisting of
i) hydrogen and
ii) halogen;

$R^3$ is selected from the group consisting of
i) hydrogen and
ii) $C_{1-6}$-alkyl;

$R^4$ is selected from the group consisting of
i) hydrogen,
ii) halogen, and
iii) $C_{1-6}$-alkyl;

$R^5$ is selected from the group consisting of
i) hydrogen,
ii) halogen, and
iii) $C_{1-6}$-alkyl;

or a pharmaceutically acceptable salt thereof.

2. A compound of claim 1 having formula Ia,

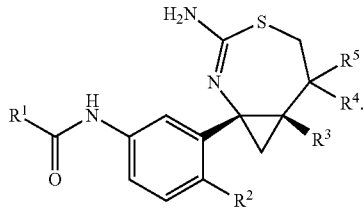

3. The compound of claim 1, wherein $R^1$ is heteroaryl substituted by 1-2 substituents individually selected from cyano and halogen.

4. The compound of claim 3, wherein $R^1$ is pyridinyl substituted by 1-2 substituents individually selected from cyano and chloro.

5. The compound of claim 1, wherein $R^2$ is hydrogen.

6. The compound of claim 1, wherein $R^2$ is halogen.

7. The compound of claim 1, wherein $R^2$ is F.

8. The compound of claim 1, wherein $R^3$ is hydrogen.

9. The compound of claim 1 wherein $R^4$ is hydrogen.

10. The compound of claim 1, wherein $R^5$ is hydrogen.

11. The compound of claim 1, selected from the group consisting of

5-Chloro-pyridine-2-carboxylic acid [3-((1SR,7SR)-3-amino-4-thia-2-aza-bicyclo[5.1.0]oct-2-en-1-yl)-4-fluoro-phenyl]-amide, 5-Chloro-pyridine-2-carboxylic acid [3-((1S,7S)-3-amino-4-thia-2-aza-bicyclo[5.1.0]oct-2-en-1-yl)-4-fluoro-phenyl]-amide, 5-Cyano-pyridine-2-carboxylic acid [3-((1S,7S)-3-amino-4-thia-2-aza-bicyclo[5.1.0]oct-2-en-1-yl)-4-fluoro-phenyl]-amide, N-(3-((1S,7S)-3-Amino-4-thia-2-azabicyclo[5.1.0]oct-2-en-1-yl)phenyl)-5-chloropicolinamide, N-(3-((1S,7S)-3-Amino-4-thia-2-azabicyclo[5.1.0]oct-2-en-1-yl)phenyl)-5-cyanopicolinamide, N-(3-((1SR,7SR)-3-amino-4-thia-2-azabicyclo[5.1.0]oct-2-en-1-yl)-4-chlorophenyl)-5-chloropicolinamide, N-(3-((1SR,7SR)-3-Amino-4-thia-2-azabicyclo[5.1.0]oct-2-en-1-yl)phenyl)-5-chloropicolinamide, and N-(3-((1SR,7SR)-3-Amino-4-thia-2-azabicyclo[5.1.0]oct-2-en-1-yl)phenyl)-5-cyanopicolinamide, or a pharmaceutically acceptable salt thereof.

12. The compound of claim 1, selected from the group consisting of

N-(3-((1SR,7SR)-3-Amino-4-thia-2-azabicyclo[5.1.0]oct-2-en-1-yl)phenyl)-5-chloropicolinamide and N-(3-((1S,7S)-3-Amino-4-thia-2-azabicyclo[5.1.0]oct-2-en-1-yl)phenyl)-5-chloropicolinamide, or a pharmaceutically acceptable salt thereof.

13. A pharmaceutical composition comprising a therapeutically effective amount of a compound of formula I

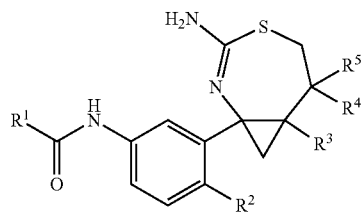

wherein $R^1$ is selected from the group consisting of
iii) heteroaryl and
iv) heteroaryl substituted by 1-2 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkenyl, $C_{2-6}$-alkynyl and $C_{1-6}$-alkyl;

$R^2$ is selected from the group consisting of
iii) hydrogen and
iv) halogen;

$R^3$ is selected from the group consisting of
iii) hydrogen and
iv) $C_{1-6}$-alkyl;

$R^4$ is selected from the group consisting of
iv) hydrogen,
v) halogen, and
vi) $C_{1-6}$-alkyl;

$R^5$ is selected from the group consisting of
iv) hydrogen,
v) halogen, and
vi) $C_{1-6}$-alkyl;

or a pharmaceutically acceptable salt thereof and a pharmaceutically acceptable carrier.

* * * * *